United States Patent
Wolter et al.

(10) Patent No.: US 6,222,055 B1
(45) Date of Patent: Apr. 24, 2001

(54) HYDROLYZABLE AND POLYMERIZABLE AND/OR POLYADDITIVE SILANES

(75) Inventors: Herbert Wolter, Tauberbischofsheim; Werner Storch, Hoechberg, both of (DE)

(73) Assignee: Fraunhofer-Gesellschaft zur Foerderung der angwandten Forschung e.V., Munich (DE)

( * ) Notice: Subject to any disclaimer, the term of this patent is extended or adjusted under 35 U.S.C. 154(b) by 0 days.

(21) Appl. No.: 09/399,301

(22) Filed: Sep. 17, 1999

Related U.S. Application Data

(63) Continuation-in-part of application No. 08/793,705, filed on Mar. 3, 1997, now abandoned.

(30) Foreign Application Priority Data

Jul. 6, 1995 (DE) ................................. 195 24 657

(51) Int. Cl.[7] .................. C07F 7/10; C07F 7/08
(52) U.S. Cl. .............. 556/413; 556/419; 556/420; 556/437; 556/440
(58) Field of Search .................. 556/413, 437, 556/440, 420, 419

(56) References Cited

U.S. PATENT DOCUMENTS 5,717,125 * 2/1998 Wolter et al. .................. 556/413 X \* cited by examiner Primary Examiner—Paul F. Shaver
(74) Attorney, Agent, or Firm—Karl Hormann

(57) ABSTRACT

Hydrolysable and polymerizable or polyadditive silanes and methods of their production and the production of (hetero) silicic acid polycondensates or of polymers. The silanes in accordance with the invention are of general formula

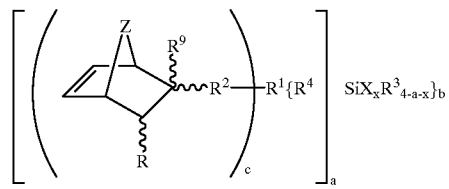

in which the groups and indices are equal or different and have the following meaning:

R=hydrogen, $R^2-R^1-R^4-SiX_xR^3_{3-x}$, carbonyl, alkyl, alkenyl, aryl, alkylaryl or arylalkyl;

$R^1$=alkylene, arylene, arylenealkene or alkenearylene;

$R^2$=alkylene, arylene, arylenealkene or alkenearylene;

$R^3$=Alkyl, alkenyl, aryl, alkylaryl or arylalkyl;

$R^4$=—$(CHR^6—CHR^6)_n$—, where n=0 or 1, —$CHR^6$—$CHR^6$—S—$R^5$—; —CO—S—$R^5$—, —$CHR^6$—$CHR^6$—$NR^6R^5$—, —Y—CS—NH—$R^5$—, —S—$R^5$—, —Y—CO—NH—$R^5$—, —CO—O—$R^5$—, —Y—CO—$C_2H_3$(COOH)—$R^5$—, —Y—CO—$C_2H_3$(OH)—$R^5$— or —CO—$NR^6$—$R^5$—;

$R^5$=alkene, arylene, arylenealkene or alkenearylene;

$R^6$=hydrogen, alkyl or aryl with 1 to 10 carbon atoms;

$R^9$=hydrogen, alkyl, alkene, aryl, alkylaryl or arylalkyl;

X=hydrogen, halogen, hydroxy, alkoxy, acyloxy, alkylcarbonyl, alkoxycarbonyl or NR"$_2$, where R"=hydrogen, alkyl or aryl;

Y=—O—, —S— or —$NR^6$—;

Z=—O— or —$(CHR^6)_m$—, where m=1 or 2;

a=1, 2 or 3, with b=1 for a=2 or 3;

b=1, 2 or 3, with a=1 for b=2 or 3;

c=1 to 6;

x=1, 2 or 3;

a+x=2, 3 or 4.

24 Claims, No Drawings

HYDROLYZABLE AND POLYMERIZABLE AND/OR POLYADDITIVE SILANES

This is a Continuation-in-Part of application Ser. No.: 08/793,705 filed Mar. 3, 1997 now abandoned.

BACKGROUND OF THE INVENTION

1. Field of the Invention

The invention relates to hydrolyzable and polymerizable and/or polyadditive silanes, to processes of their production and their use in the production of organically modified silicic acid polycondensates and/or hetero polycondensates, as well as to their use in the production of macromolecular compounds by polymerization and/or polyaddition.

2. The Prior Art

Hydrolyzable organically modified silanes are widely used in the manufacture of scratch-proof coatings for the most variegated substrates, in the production of fillers, of adhesive and caulking compounds, or of molded arcticles. In such processes, the silanes are hydrolytically condensed either by themselves, in mixtures or in the presence of further hydrolyzable and/or condensable components, with final curing being accomplished thermically, photochemically, or by redox induction.

Thus, scratch-proof layers are known from DE 3 407 087, which are formed by a hydrolytic condensation of a mixture consisting, among others, of a hydrolyzable titanium or zirconium compound and of a hydrolyzable organo-functional silane $R'_m(R''Y)_n SiX_{(4-m-n)}$ in which R' is, for instance, an alkyl or alkenyl, R" is, for instance, an alkene or alkenylene and X is a hydrolyzable group.

From DE 3,536,716 A1, adhesive and caulking compounds, for instance, are known which have been made by hydrolytic condensation of one or more organo-silanes of the general formula $R_m SiX_{4-m}$ and, where desired, of one or more of components like $SiX_4$ and/or $R_n(R''Y)_p SiX_{4-n-p}$, where R and R" are, for instance, an alkyl, alkenyl, aryl, alkylaryl, arylalkyl, alkenylaryl or arylalkenyl, X is, for instance, hydrogen, halogen, hydroxy, alkoxy or acyloxy, and where Y is, for instance, a halogen or a possibly substituted amino, amide, aldehyde, alkylcarbonyl, carboxy, hydroxy, mercapto or cyano group.

Furthermore, commercial silanes with reactive double bonds are known, as, for example, (meth)acryloxysilanes of the following type,

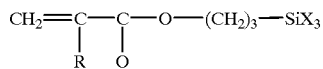

where R is hydrogen or methyl and X is, for instance, a halogen or alkoxy. These silanes are hydrolyzable and polymerizable and may be used for producing the above-mentioned systems. They offer the great advantage that the resultant coating, the resultant filler, adhesive or caulking compound or the resulatant molded article may be cured thermically, photochemically or by redox induction by polymerization at the double bonds.

Commercial silanes with reactive double bonds, such as, for instance, the (meth)acryloxysinales referred to above, generally are monofunctional compounds with a C=C double bond, and are usually low molecular and thus, prior to the Si—X hydrolysis and condensation, relatively volatile compounds which give rise to toxicological concerns because of their acryl group. During further processing by polymerization or modified functionalization these silanes suffer from the further disadvantage that because of the single reactive C=C double bond only chain polymers can be produced and that with prior functionalization, the C=C double bond required for the organic polymerisation is usually lost. Furthermore, a short chain only is usually present between the double bond and the silicon capable of forming an anorganic network, so that on the basis of the organic groups the mechanical characteristics (flexibility, etc.) may be varied within very narrow limits only.

While hydrolyzable and polymerizable silanes provided in their molecule with a norbornene group are known from EP 0,388,028 A2 and EP 0,439,650 A1, there is still a need for improvements, including in respect of a functionalization of the molecule.

OBJECTS OF THE INVENTION

It is, therefore, an object of the present invention to provide novel organically modified silanes which are hydrolyzable and polymerizable and/or polyadditive and which by themselves, in mixtures, or together with other hydrolyzable, condensible, polyadditive or polymerizable components may be processed into scratch-proof coatings, filling, adhesive or caulking compounds, molded articles, foils or fibers, fillers or additives. Such silanes are to be universally applicable, and they should be incorporable into an anorganic-organic compound system, i.e., into an anorganic-organic network. Furthermore, these silanes are to be producible in a quick and simple manner, i.e., without requiring an elaborate synthesizing process. Moreover, the space between the silicon and reactive double bond should be arbitrarily settable. The silanes are also to be provided with a variable number of C=C double bonds, and additional functionalities should be incorporable into the molecule.

SUMMARY OF THE INVENTION

The object is accomplished by hydrolyzable and polymerizable and/or polyadditive silanes of the general Formula I:

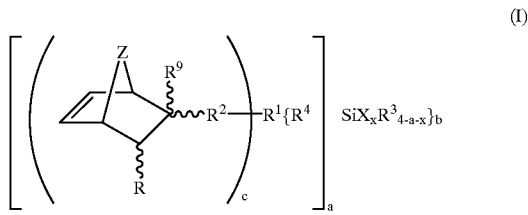

in which the groups and indices are equal or dissimilar and in which

R=hydrogen, $R^2$—$R^1$—$R^4$—$SiX_x R^3_{3-x}$, carboxyl, alkyl, alkenyl, aryl, alkylaryl or arylalkyl each having 1 to 15 carbon atoms, wherein these groups may contain oxygen or sulfur atoms, ester, carbonyl, amide or amino groups;

$R^1$=alkene, arylene, arylenealkene or alkenearylene each having 0 to 15 carbon atoms, wherein these groups may contain oxygen or sulfur atoms, ester, carbonyl, amide, or amino groups;

$R^2$=alkene, arylene, arylenealkene or alkenearylene each having 0 to 15 carbon atoms, wherein these groups may contain oxygen or sulfur atoms, ester, carbonyl, amide, or amino groups;

$R^3$=alkyl, alkenyl, aryl, alkylaryl or arylalkyl each having 1 to 15 carbon atoms, wherein these groups may contain oxygen or sulfur atoms, ester, carbonyl, amide or amino groups;

$R^4$=—$(CHR^6$—$CHR^6)_n$-, where n=0 or 1, —$CHR^6$—$CHR^6$—S—$R^5$—, —CO—S—$R^5$—, $CHR^6$—$CHR^6$—$NR^6$—$R^5$—, —Y—CS—NH—$R^5$—, —S—$R^5$, —Y—CO—NH—$R^5$—, —CO—O—$R^5$—, —Y—CO—$C_2H_3$(COOH)—$R^5$—, —Y—CO—$C_2H_3$(OH)—$R^5$— or —CO—$NR^6$—$R^5$;

$R^5$=alkene, arylene, arylenealkene or alkenearylene each having 1 to 15 carbon atoms, wherein these groups may contain oxygen or sulfur atoms, ester, carbonyl, amide, or amino groups;

$R^6$=hydrogen, alkyl or aryl with 1 to 10 carbon atoms;

$R^9$=hydrogen, alkyl, alkenyl, aryl, alkylaryl or arylalkyl each having 1 to 15 carbon atoms, wherein these groups may contain oxygen or sulfur atoms, ester, carbonyl, amide, or amino groups;

X=hydrogen, halogen, hydroxy, alkoxy, acyloxy, alkylcarbonyl, alkoxycarbonyl or $NR''_2$ wherein R''=hydrogen, alkyl or aryl;

Y=—O—, —S— or —$NR^6$—;

Z=—O— or —$(CHR^6)_m$— wherein m=1 or 2;

a=1, 2 or 3, with b=1 if a=2 or 3;

b=1, 2 or 3, with a=1 if b=2 or 3;

c=1 to 6;

x=1, 2 or 3;

a+x=2, 3 or 4.

The following silanes are prior art and are excluded from the protection sought:

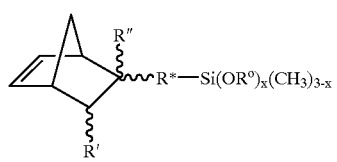

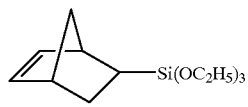

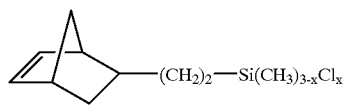

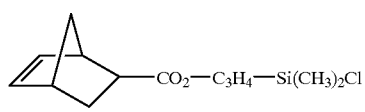

The groups and indices are:

R'=hydrogen, methyl or ethyl;

R''=hydrogen, methyl or ethyl;

R*=organic group having 1 to 6 carbon atoms;

R°=alkyl or acyl having 1 to 6 carbon atoms;

x=1, 2 or 3.

Also known are the compounds:

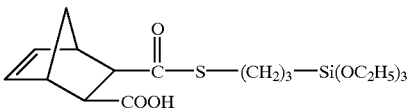

(A)

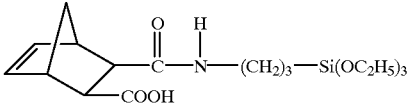

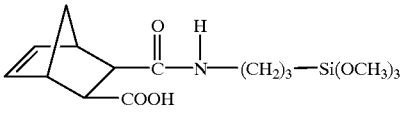

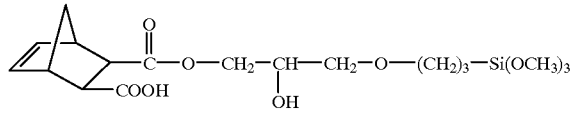

Also, compounds of the general formulae are excluded from the protection sought:

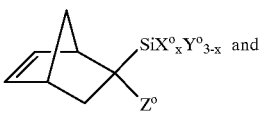

(B)

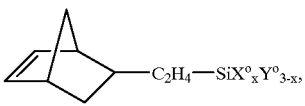

in which the rests are as follows:

X°=hydrolyzable group;

Y°=monovalent organic group bound to an Si by a C atom;

Z°=hydrogen or —$CH_2$—$CH_3$. - - - ;

Furthermore, the following compounds are excluded from the protection sought:

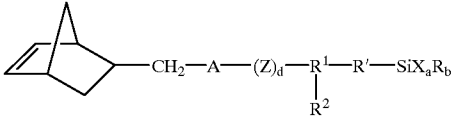

(C)

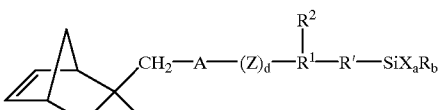

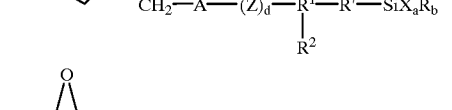

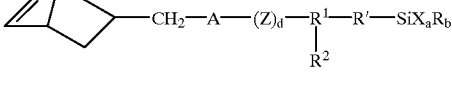

-continued

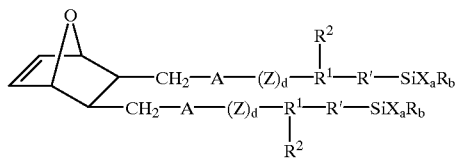

wherein:
- A=O, S, or NH if d=1 and Z=CO and $R^1$=alkylene, arylene or alkylenearylene each with 1 to 10 carbon atoms, whereby these rests may be interrupted by oxygen and sulphur atoms or by amino groups, and $R^2$=COOH; or
- A=O, S, or NH if d=1 and Z=CO and $R^1$=alkylene, arylene or alkylenearylene each with 1 to 10 carbon atoms, whereby these rests may be interrupted by oxygen and sulphur atoms or by amino groups, and $R^2$=H; or
- A=O, S, NH or COO if d=1 and Z=CHR with R=H, alkyl, aryl, alkylaryl, and $R^1$=alkylene, arylene or alkylenearylene each with 1 to 10 carbon atoms, whereby these rests may be interrupted by oxygen and sulphur atoms or by amino groups, and $R^2$=OH; or
- A=O, S, or NH if d=1 and Z=CO and $R^1$=alkylene, arylene or alkylenearylene each with 1 to 10 carbon atoms, whereby these rests may be interrupted by oxygen and sulphur atoms or by amino groups, and $R^2$=H; or
- A=O, S, NH or COO if d=1 and Z=CHR with R=H. alkyl, aryl, alkylaryl, and $R^1$=alkylene, arylene or alkylenearylene each with 1 to 10 carbon atoms, whereby these rests may be interrupted by oxygen and sulphur atoms or by amino groups, and $R^2$=OH; or
- A=O, S, NH or COO if d=0 and $R^1$=alkylene, arylene or alkylenearylene each with 1 to 10 carbon atoms, whereby these rests may be interrupted by oxygen and sulphur atoms or by amino groups, and $R^2$=OH; or
- A=S if d=1 and
- Z=CO and
- $R^1$=N and
- $R^2$=N;
- a=1,2 or 3;
- b=0,1 or 2;
- a+b=3;
- c=1,2,3 or 4. - - - ;

The silanes of Formula I are polyadditive, for instance, to thiols, by way of the C═C double bonds of the norbornene, oxabicycloheptene and/or bicyclooctene groups, and ring-scission polymerizable, and they are hydrolyzable by way of the X groups. An anorganic network with Si—O—Si-units may be formed by way of the hydrolyzable groups, whereas the C═C double bonds contained in the bicyclic groups may be subjected to a polymerization or polyaddition to an an organic network.

The alkyl groups of general Formula I may be straight chain, cross-linked, cyclic or bicyclic groups arylene or alkylenearylene each with 1 to 10 carbon atoms, whereby these rests may be interrupted by oxygen and sulphur atoms or by amino groups, and $R^2$=H; or
- A=O, S, NH or COO if d=1 and Z=CHR with R=H, alkyl, aryl, alkylaryl, and $R^1$=alkylene, arylene or alkylenearylene each with 1 to 10 carbon atoms, whereby these rests may be interrupted by oxygen and sulphur atoms or by amino groups, and $R^2$=OH; or
- A=O, S, NH or COO if d=0 and $R^1$=alkylene, arylene or alkylenearylene each with 1 to 10 carbon atoms, whereby these rests may be interrupted by oxygen and sulphur atoms or by amino groups, and $R^2$=OH; or
- A=S if d=1 and
- Z=CO and
- $R^1$=N and
- $R^2$=N;
- a=1,2 or 3;
- b=0,1 or 2;
- a+b=3;
- c=1,2,3 or 4. - - - ;

The silanes of Formula I are polyadditive, for instance, to thiols, by way of the C═C double bonds of the norbornene, oxabicycloheptene and/or bicyclooctene groups, and ring-scission polymerizable, and they are hydrolyzable by way of the X groups. An anorganic network with Si—O—Si-units may be formed by way of the hydrolyzable groups, whereas the C═C double bonds contained in the bicyclic groups may be subjected to a polymerization or polyaddition to an an organic network.

The alkyl groups of general Formula I may be straight chain, cross-linked, cyclic or bicyclic groups bromine, and especially chlorine.

Where a, b, c or x≧2, the X and R groups may respectively be identical or dissimilar.

Preferred embodiments of silanes in accordance with the invention are of the general Formulae II, III, IV, V, VI or VII, that is to say, the indices a and/or b and/or c of general Formula I equal 1. The remaining groups and indices are defined as in Formula I.

(II)

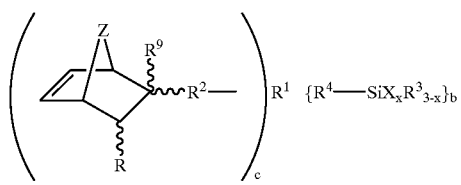

(III)

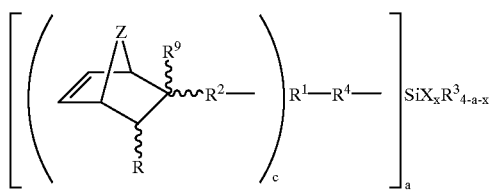

(IV)

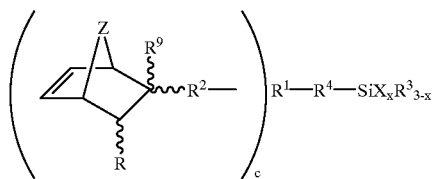

(V)

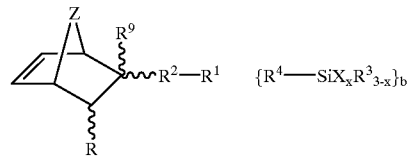

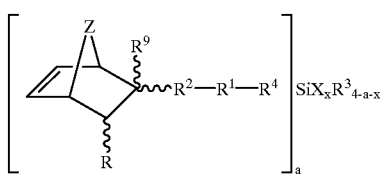
(VI)
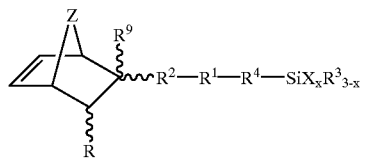
(VII)
Without restricting generality, concrete examples of groups with an a index hereafter set forth, wherein these groups may be present more than once in a molecule.
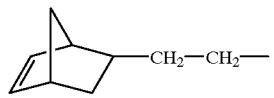
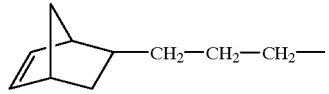
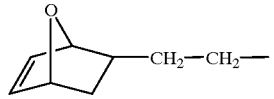
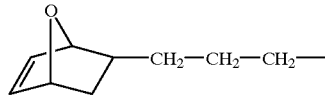
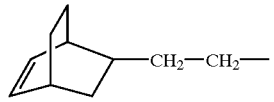
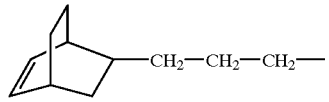
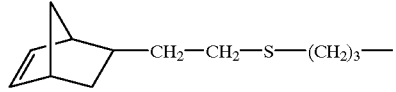
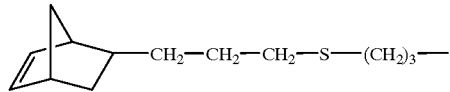
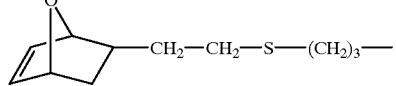
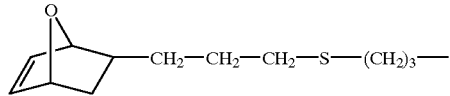
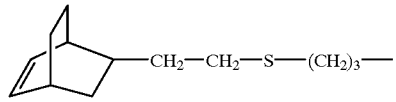
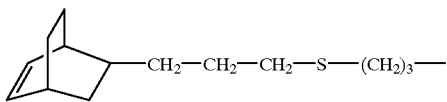
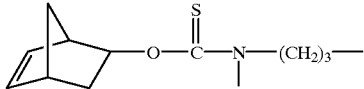
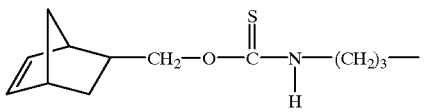
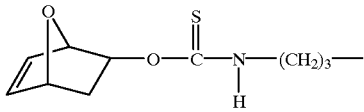
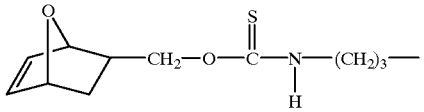
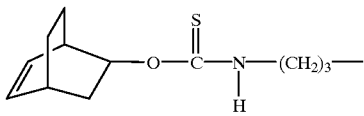
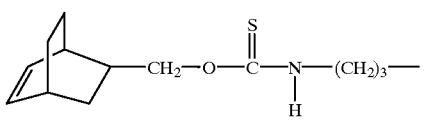
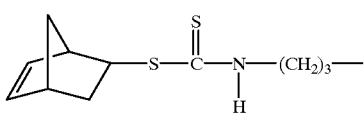
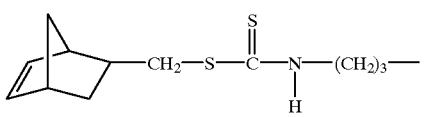
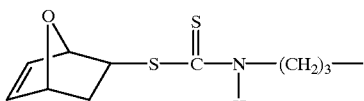
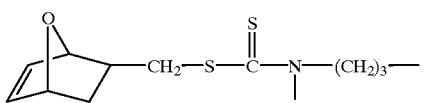
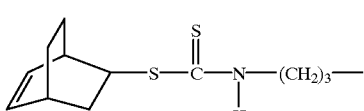
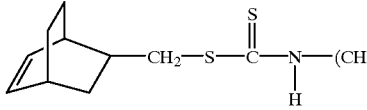
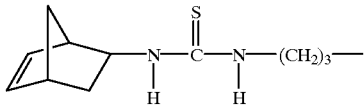

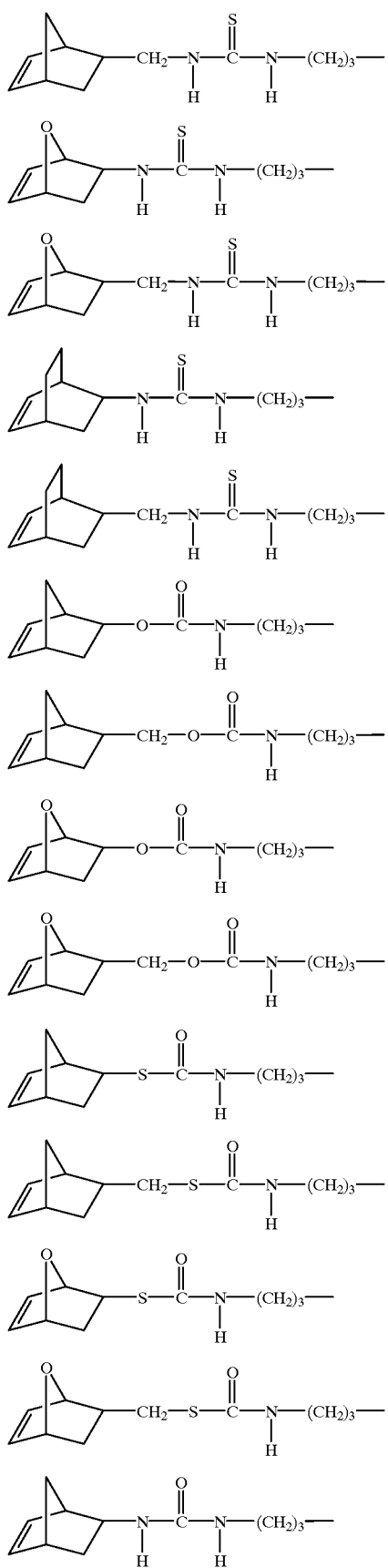
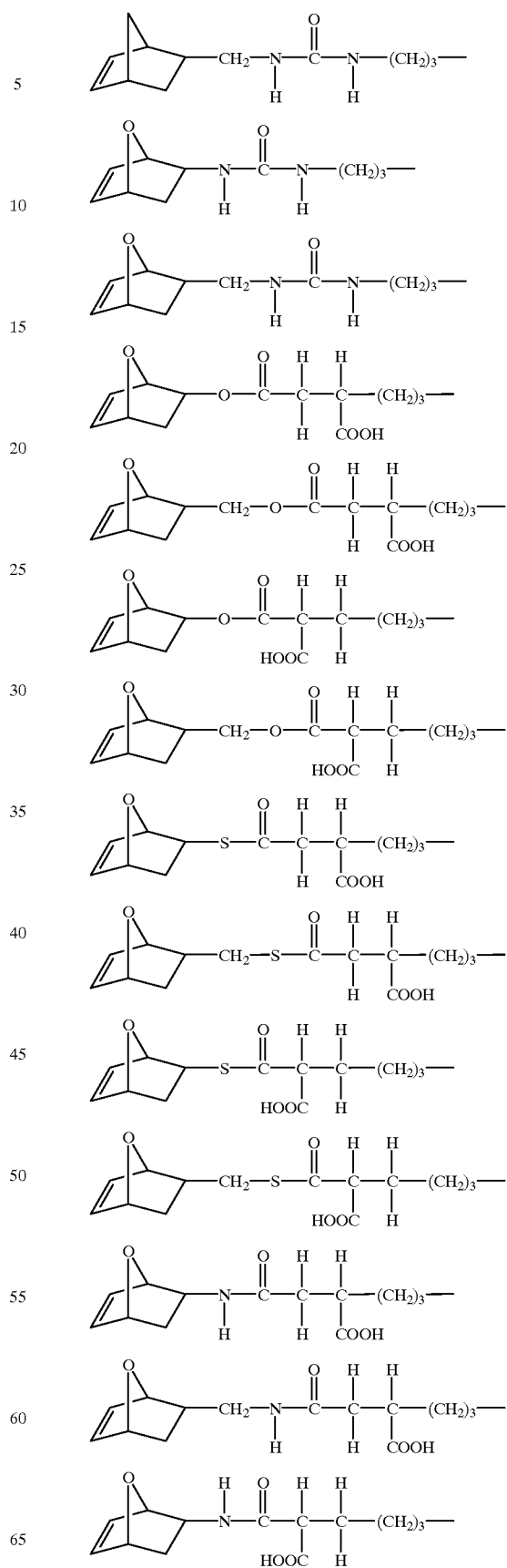

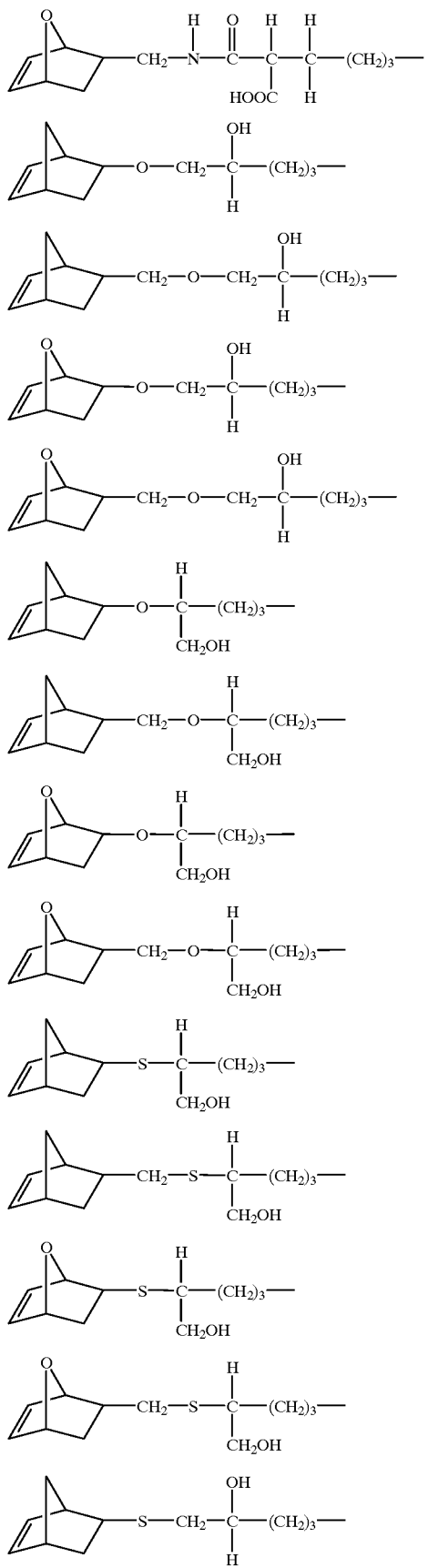
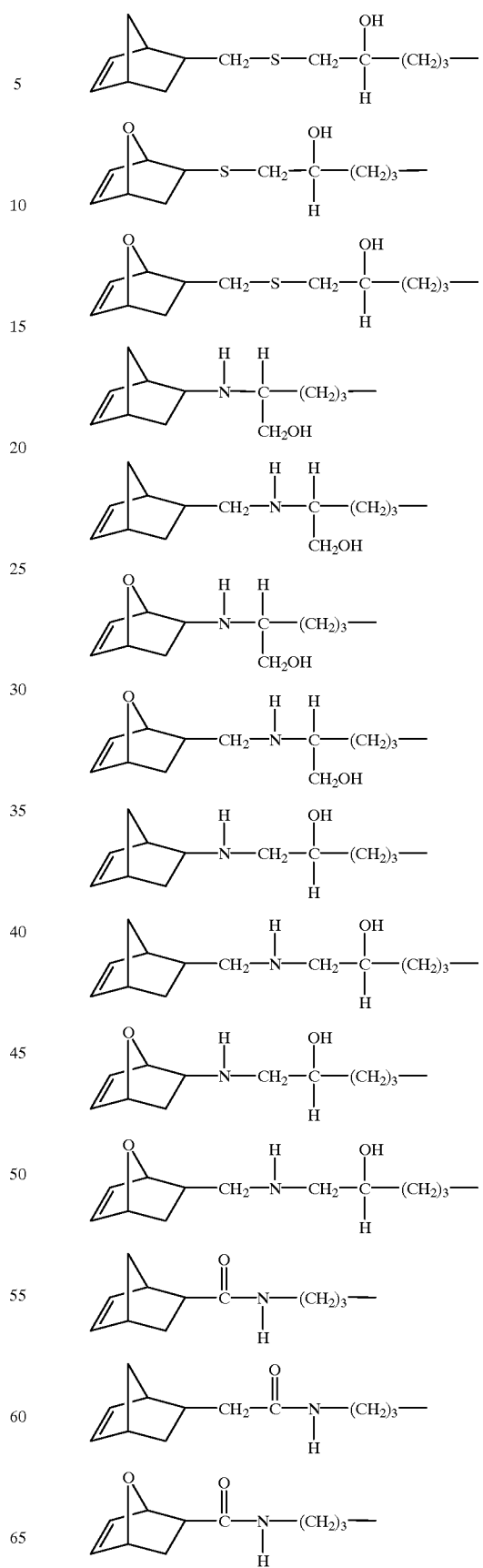

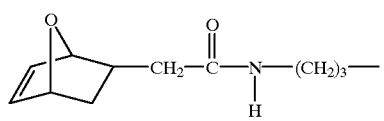
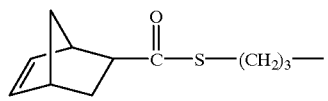
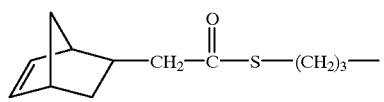
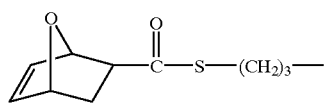
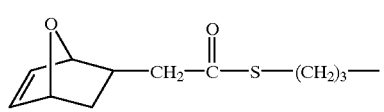
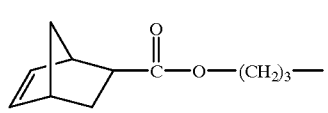
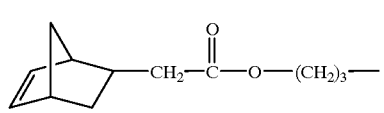
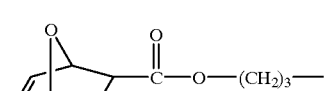
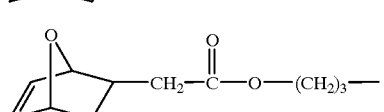
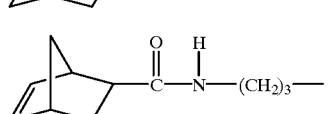
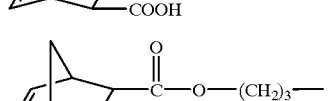
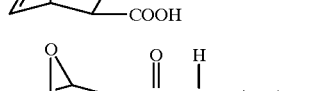
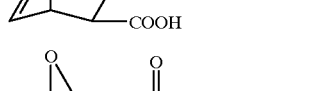
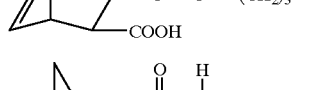
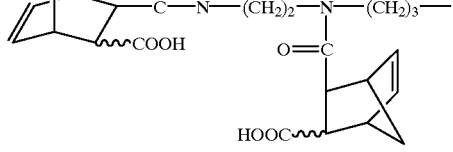
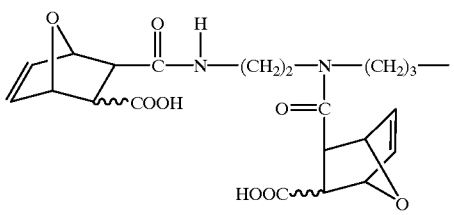
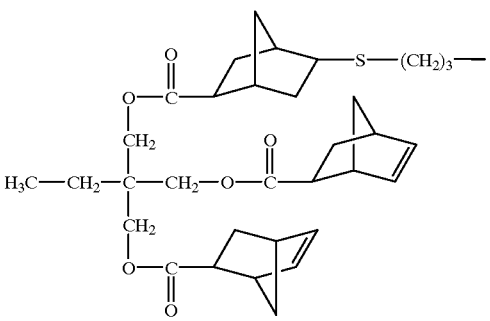
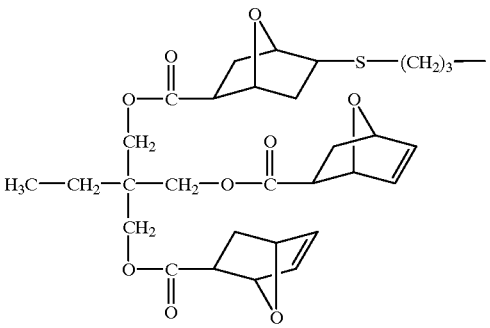
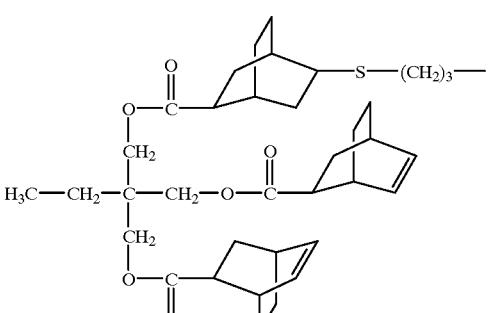
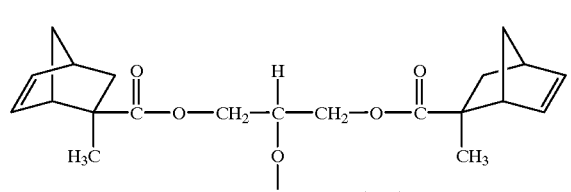
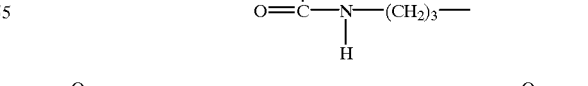
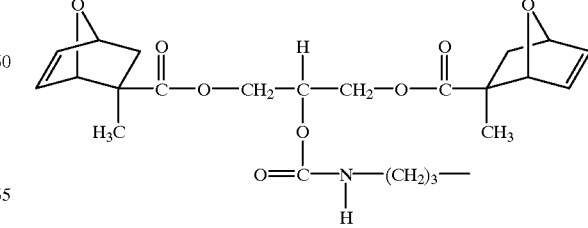

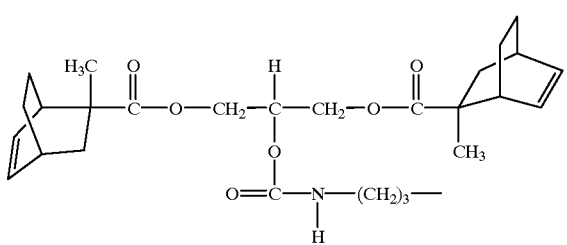
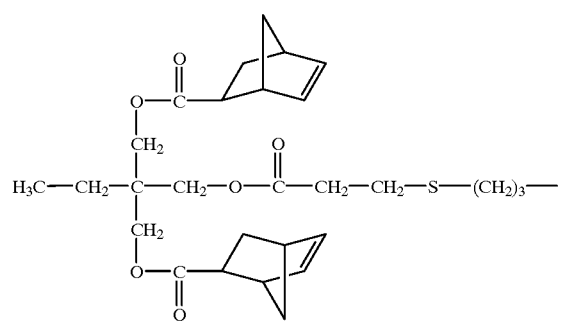
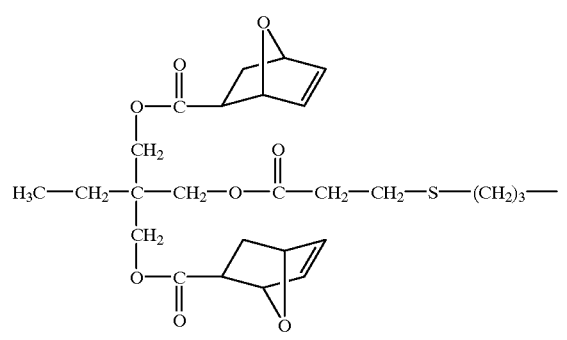
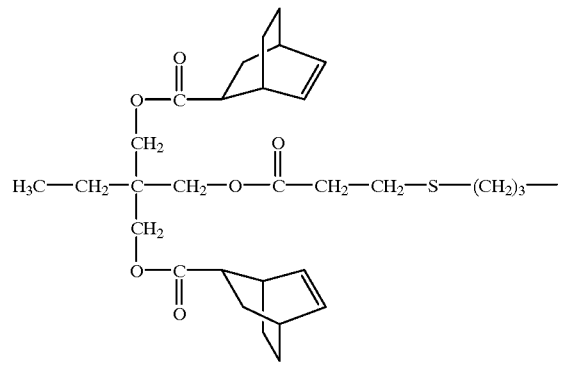
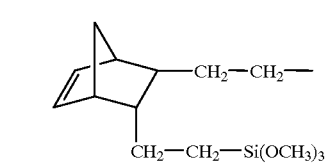
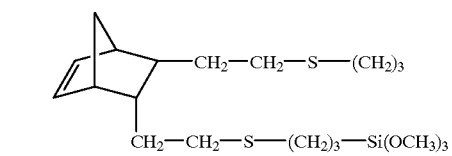
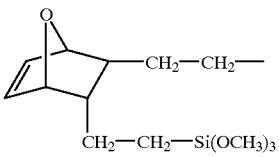
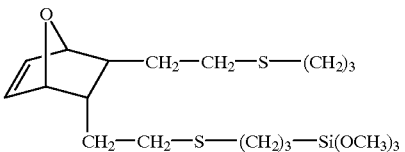
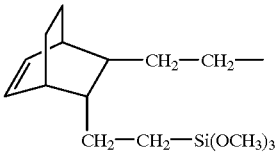
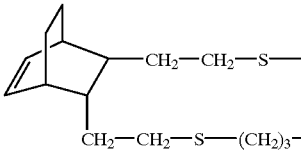
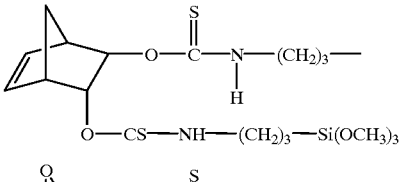
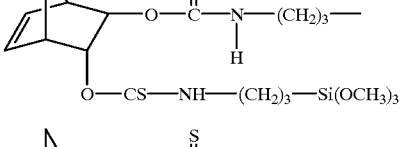
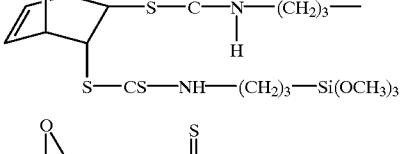
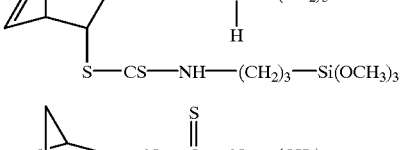
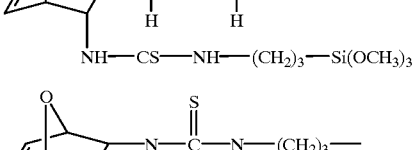
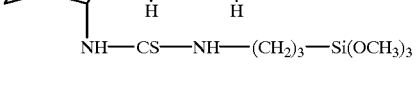

-continued

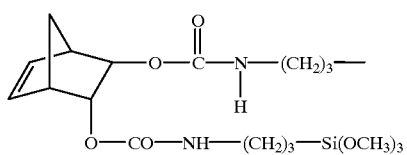

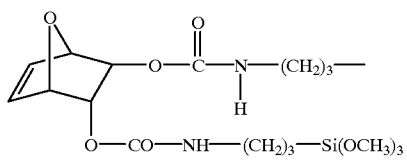

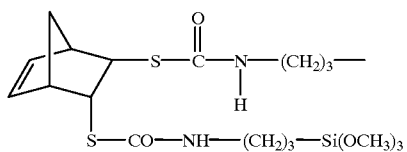

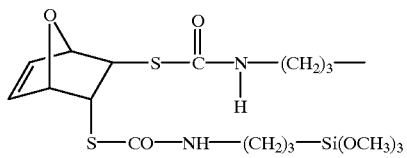

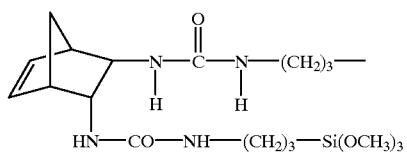

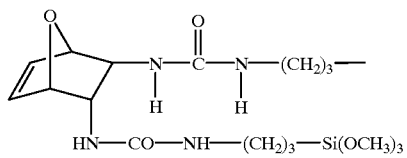

-continued

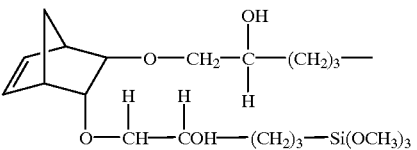

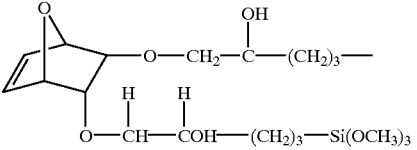

DETAILED DESCRIPTION

The silanes in accordance with the invention may be produced by a large number of additive and condensation reactions practiced in accordance with methods usual as regards these types of reaction.

In a first variant, for instance, norbornenes, oxabicycloheptenes and bicyclooctenes possessing terminal olefinic C=C double bonds, are subjected to hydrosylation, a thiol or an amine addition. The general reaction patterns are as follows, wherein the groups and indices are defined as in general Formula I. For the sake of clarity, hydrogen has been chosen for the group $R^9$ in the general reaction patterns to be hydrogen. Nevertheless, these reaction patterns remain valid in respect of the definition of group $R^9$ given in connection with general Formula I. For purposes of explanation, simple concrete examples are set forth.

Hydrosylation:

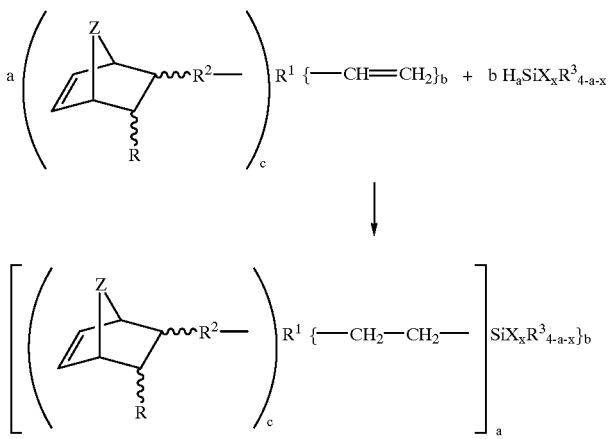

Concrete example:
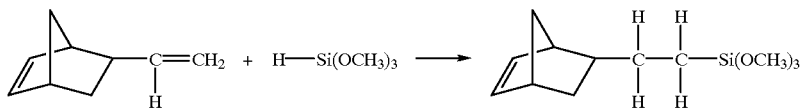
Thiol addition:
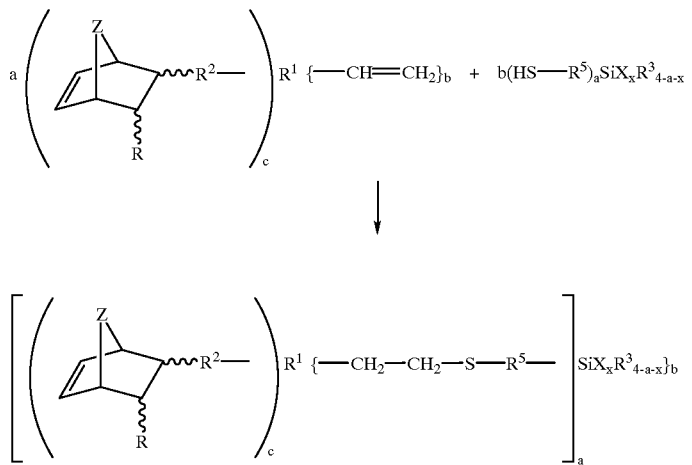
Concrete example:
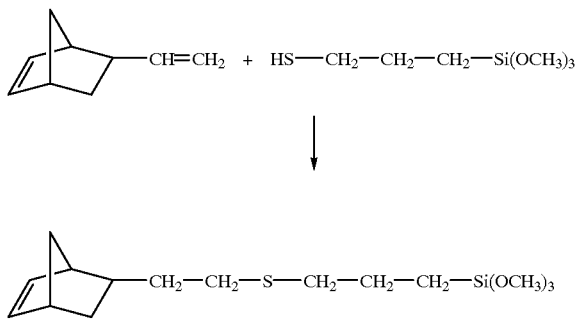
Amine addition:
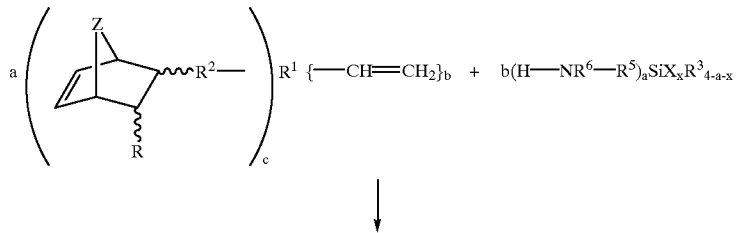

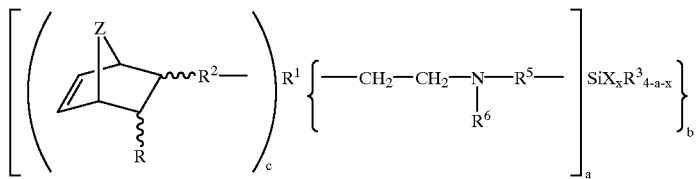

Concrete example:

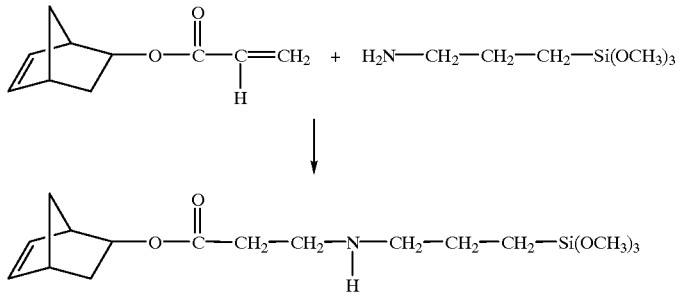

The groups $R^1$ may contain up to b terminal C=C double bonds so that up to b silane units may be added to each respective $R^1$ group. The silanes used may contain up to a hydrogen atoms, thiol or amino groups, so that up to a bicyclic groups may be added to each respective silane. Furthermore, the $R^1$ groups may each contain up to c norbornene, bicyclooctene or oxabicycloheptene units. Norbornenes and/or oxabicycloheptenes of the general Formula XV are converted analogously.

(XV)

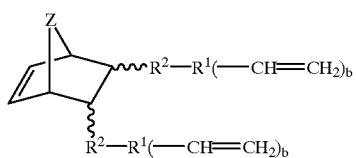

Provided $R^1$ contains at least 2 bicyclic groups, the hydrosylation, thiol or amino addition may also take place at the C=C double bonds of norbornenes, oxabicycloheptenes and bicyclooctenes.

In a further process variant bicyclic compounds containing hydroxyl, thiol or amino groups are added to silanes provided with thioisocyanate, isocyanate, anhydride or epoxy functions. The general reaction patterns have the following appearance, the groups and indices being defined as in general Formula I. As regards group $R^9$, the conditions mentioned hereinbefore pertain. Simple concrete examples are set forth for purposes of explanation.

Thioisocyanate addition:

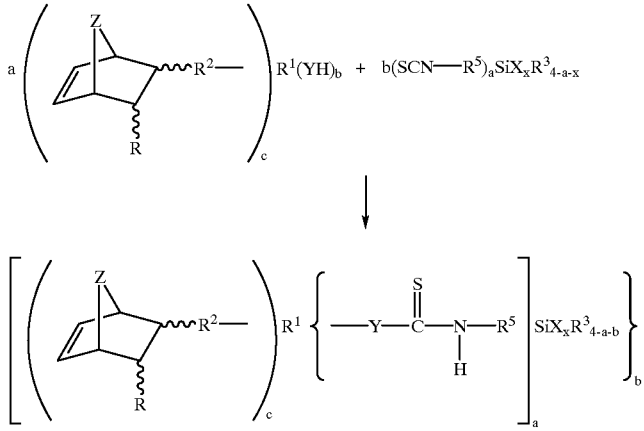

-continued
Concrete example:
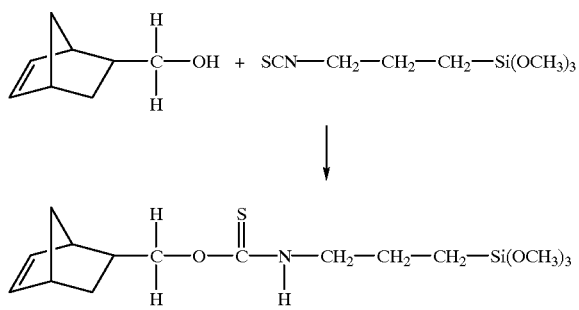
Isocyanate addition:
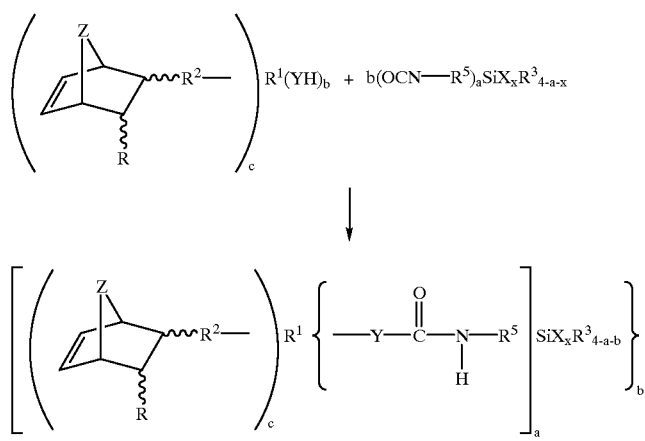
Concrete example:
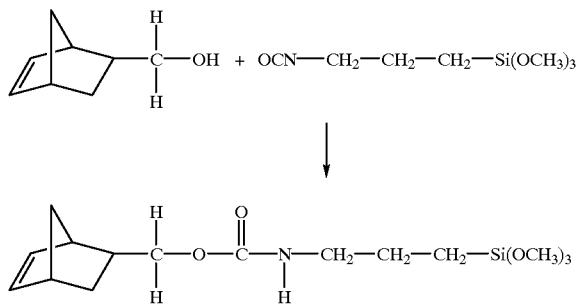
Anhydride addition:
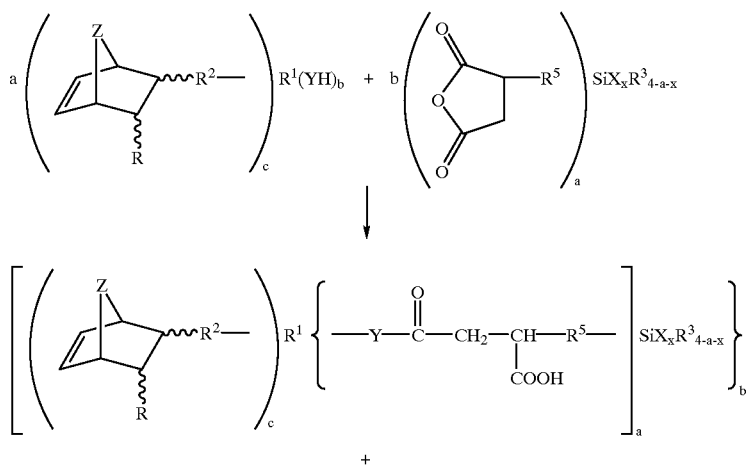
+

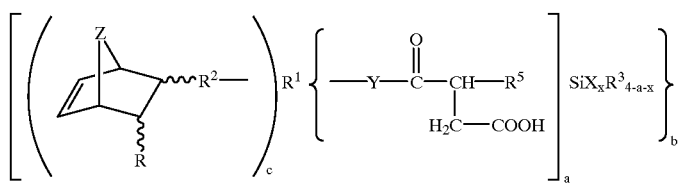
Concrete example:
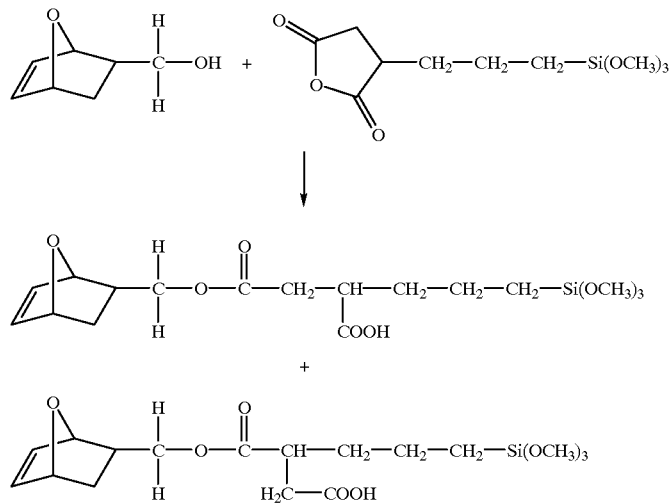
Epoxy addition:
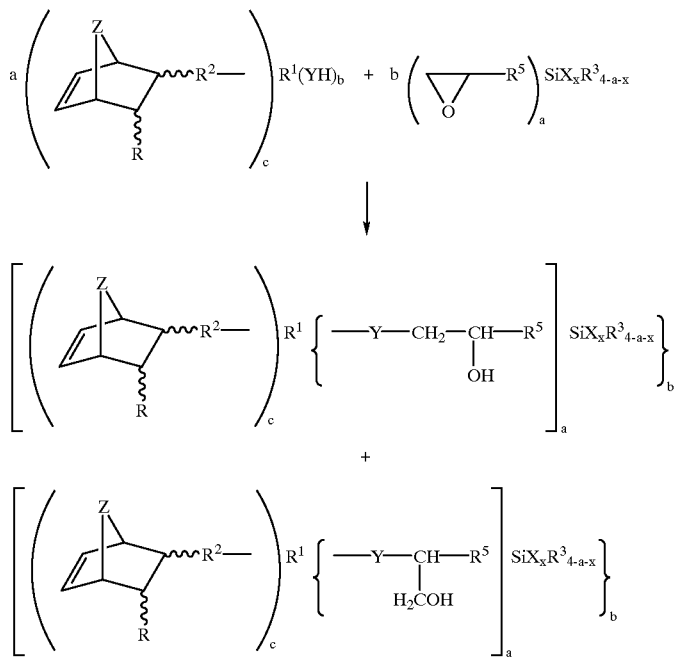
Concrete example:
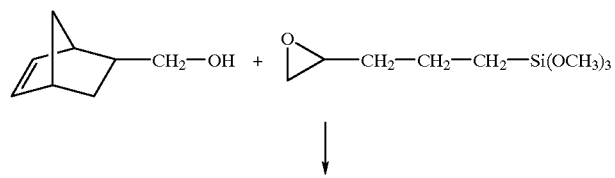

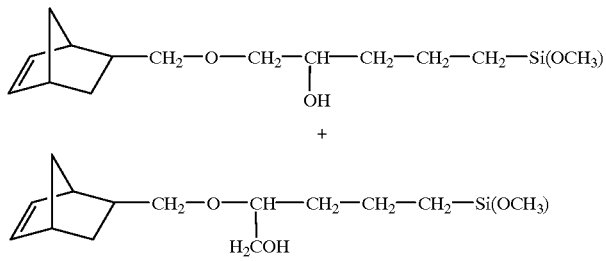

The R' group of the bicyclic components may each contain up to b hydroxyl, thiol or amino groups, so that in each case up to b silane units may be added to the $R^1$ group. The silanes used may each contain up to a thioisocyanate, isocyanate, anhydride or epoxy groups, so that up to a bicyclic groups may be added to a silane. Furthermore, the $R^1$ group may contain up to c norbornene, bicyclooctene or oxabicycloheptene units. Norbornenes, bicyclooctenes and/or oxabicycloheptenes of the general formula XVI are converted analogously.

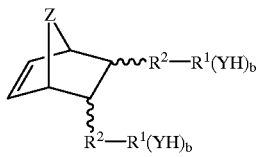

(XVI)

In further process variants, bicyclic carbonic acid derivatives are converted with silanes containing amino, thiol or hydroxyl groups. The general reaction patterns are shown hereinafter, —A connoting —OH, —Cl, —H or —OR; the remaining groups and indices being defined as in the general Formula I and for reasons of clarity R9 being hydrogen. For illustration, simple concrete examples are shown again.

Conversion with amines:

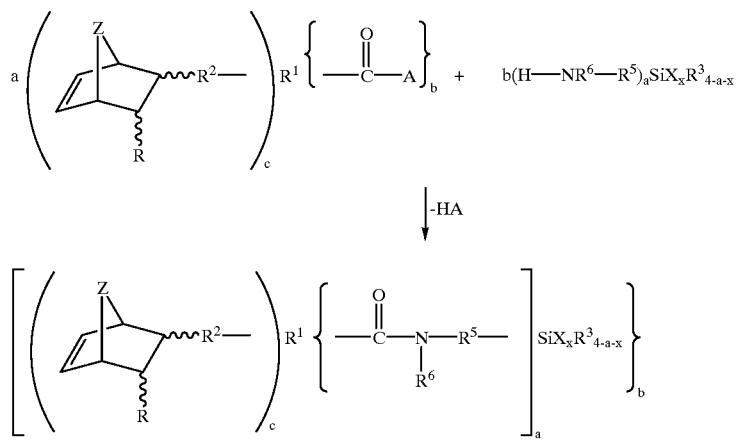

Concrete example:

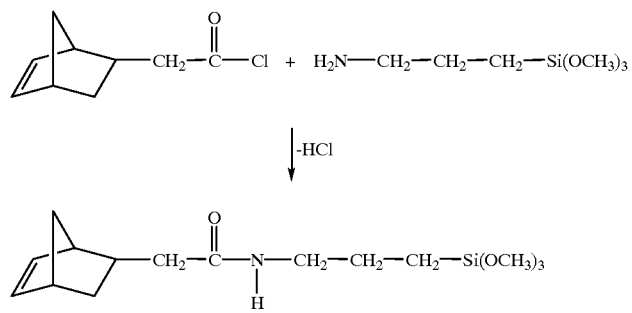

-continued
Conversion with thiols:
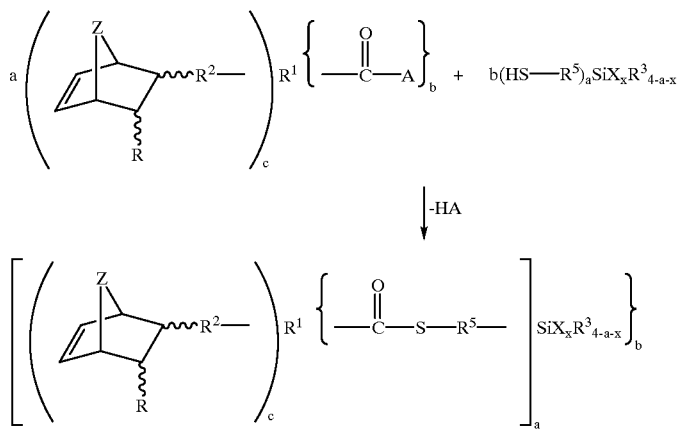
Concrete example:
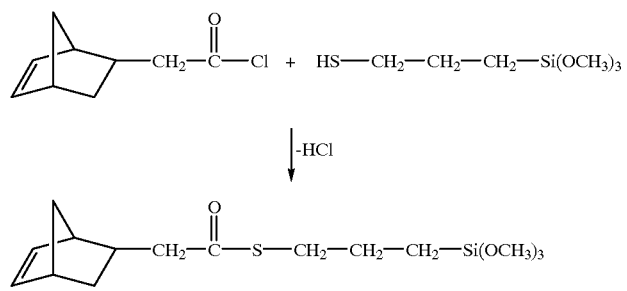
Conversion with alcohols:
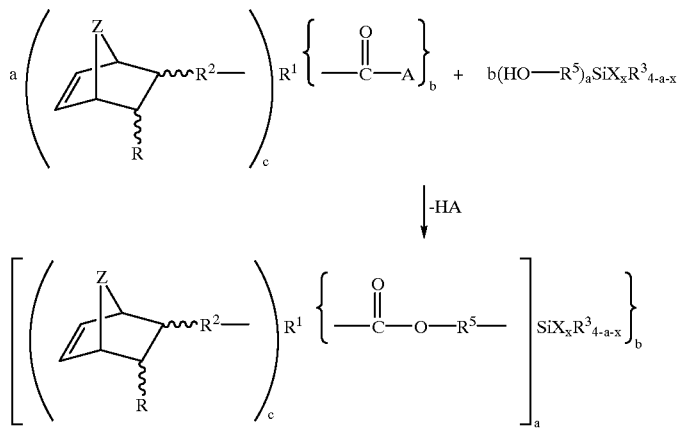
Concrete example:
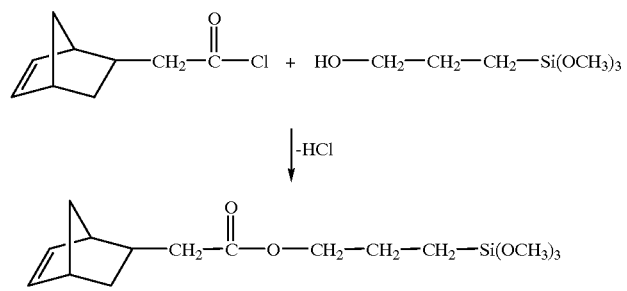

The $R^1$ group of the bicyclic components may each contain up to b carbonic acid derivatives so that in each case up to b silane units may be added to the $R^1$ group. The silanes used may each contain up to a amino, mercapto or hydroxyl groups so that up to a bicyclic groups may be added to each silane. Moreover, the $R^1$ group may contain up to c norbornene, bicyclooctene or oxabicycloheptene units. Hence, norbornenes, bicyclooctenes and/or oxabicycloheptenes of the general Formula XVII are converted analogously.

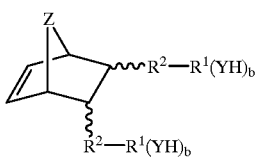

(XVII)

Further syntheses are possible by adding silanes containing amino, mercapto or hydroxyl groups to norbornenes, bicyclooctenes or oxabicyloheptenes provided with an anhydride function. The general reaction pattern is set forth hereafter. The groups and indices are defined as in the case of the general formula I, and hydrogen is set for $R^9$.

Anhydride addition:

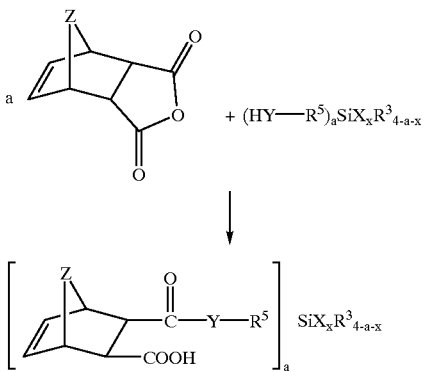

Concrete example:

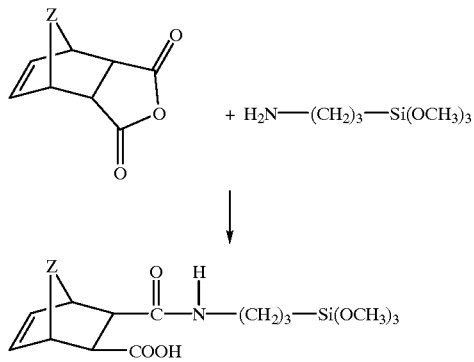

The following additions are also possible, the groups and indices being defined as in general formula I and index a being preferably >1.

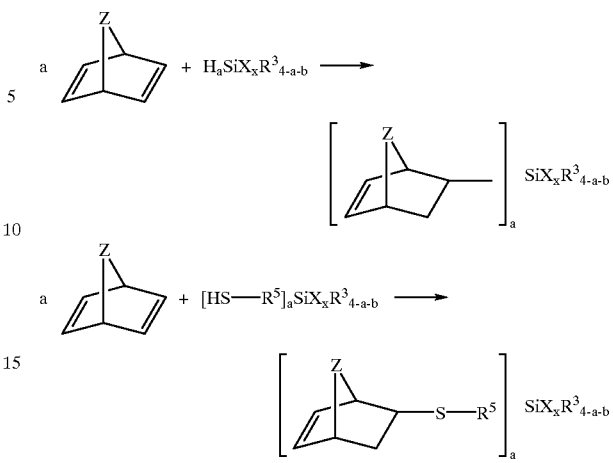

Furthermore, the bicyclic compound may be built up by a Diels-Alder addition of a furan, cyclopentadiene or cyclohexadiene derivative to an organically modified silane the organic group or groups of which are provided with one or more C═C double bonds. The general reaction patterns are as follows, with the groups and indices being defines as in general formula I and $R^9$ being hydrogen.

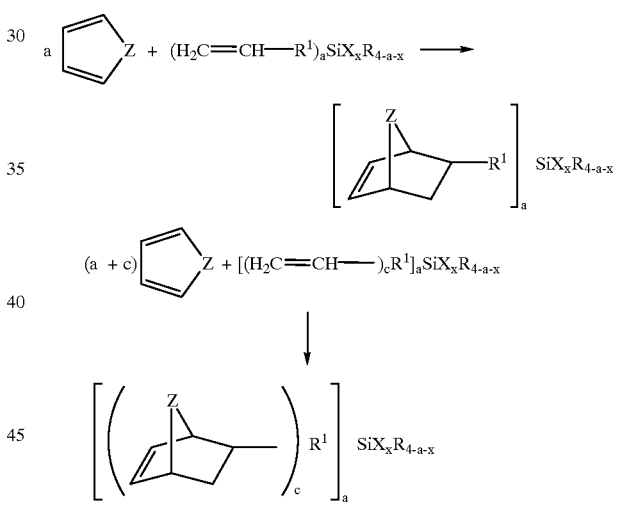

If group $R^1$ contains more than one terminal C═C double bond, more than one furan, cyclopentadiene or cyclohexadiene unit may be added.

The silanes used are commercially available, or they may be produced by processes described, for instance, in "Chemie und Technologie der Silicone" (W. Noll, Verlag Chemie GmbH., Weinheim/Bergstrasse, 1968), German Patent 4,011,044 C2 or in German Patent application P 5 4,416, 857.8.

The norbornene, bicyclooctene or oxabicycloheptene derivatives may be obtained, for instance, by the conventional functionalization of norbornadiene, bicyclooctadiene and oxabicycloheptadiene derivatives, or by a Diels-Alder addition of furan, cyclopentadiene and/or cyclohexadiene derivatives to C═C double bonds. The starting components of formula XVIII, for example, in which the groups and indices are defined as in general formula I

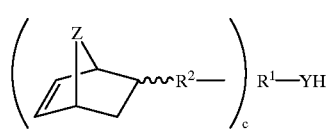

(XVIII)

may be obtained, for instance, by the folowing sequence of reactions:

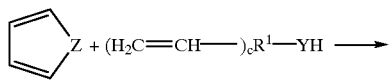

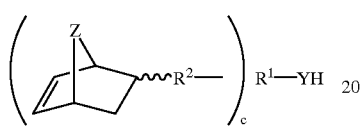

The great advantage of the production process in accordance with the invention is that organically modified silanes with a plurality of norbornene, oxabicycloheptene or bicyclohexene groups may be obtained in this manner. The following concrete examples for producing silanes with one or more bicyclic compounds in accordance with the invention are set forth without limiting generalities.

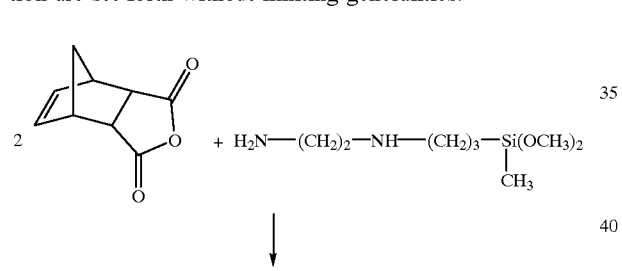

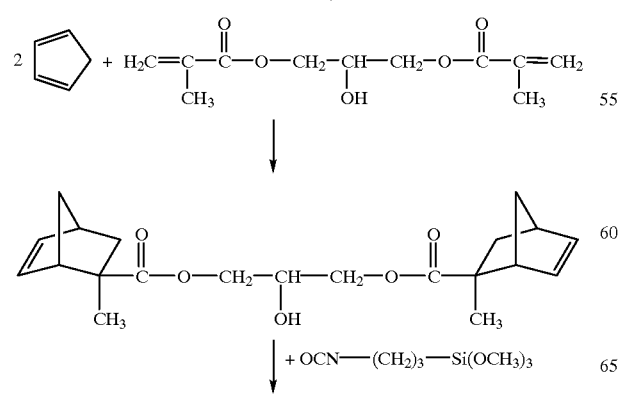

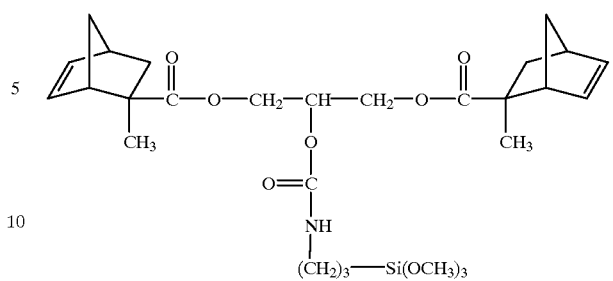

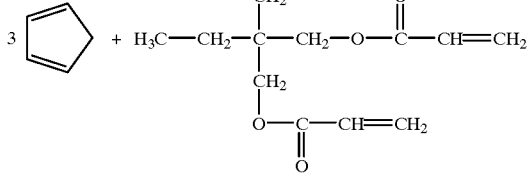

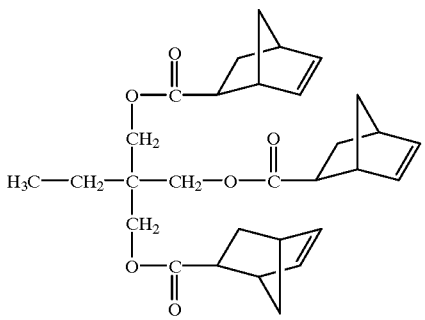

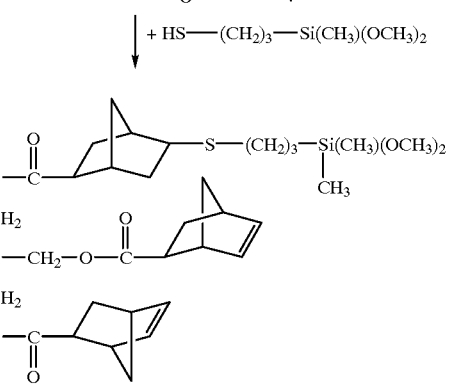

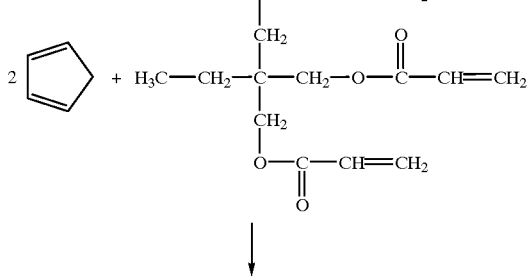

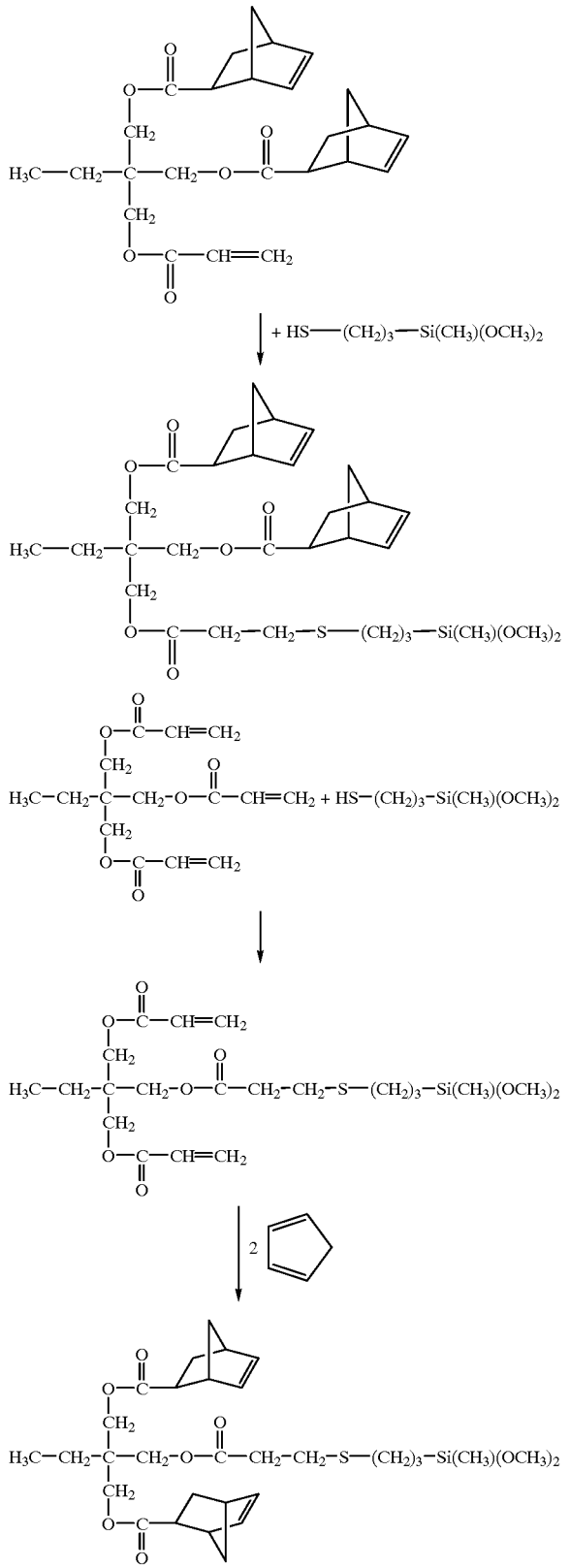

The silanes in accordance with the invention are stable substances and may be processed, either by themselves or in combination with other hydrolyzable, condensible and/or polymerizable or polyadditive components, into organically modified silicic acid polycondensates or to organically modified hetero silicic acid polycondensates the final curing of which will take place by ring scission polymerization of the C=C double bonds of the bicyclic components, or by polyaddition to thiols, for instance. However, the silanes in accordance with the invention may also be processed, either by themselves or in combination with other hydrolyzable, condensible and/or polymerizable or polyadditive componets, into polymers or polyadditive products which may be cured by subsequent hydolytic condensation.

A large number of (hetero) silicic acid polycondensates which are modified by organic groups, as well as methods of their production (proceding, for instance, on the basis of the sol-gel process from hydrolytically condensible organosilanes) are known. As mentioned hereinbefore, such condensates are used for many different purposes, e.g., as molding compounds, as laquers for coatings, etc. Yet because of the many possible uses substances of this kind, there also exists a desire to modify those condensates which are already known, on the one hand to open up new areas of applicability and, on the other hand, further to optimize their properties for certain applications.

The silanes in accordance with the invention are hydrolyzable and condensible in basic and acid environments without any resultant linking of the C=C double bonds. Thus, the silanes in accordance with the invention may by hydrolytic condensation be incorporated into an anorganic-organic network. The silanes in accordance with the invention contain hydrolyzable groups X, e.g. alkoxy groups, by means of which an anorganic network (Si—O—Si units) may be constructed, whereas the C=C double bond in the bicyclic component may be subjected to a ring-scission polimerization or to a polyaddition. It is thus possible to replace organically modified, hydrolyzable and condensible silanes in coating, filler, adhesive, casting and caulking compounds as well as in molded articles, bulk materials, composites, bonding agents, cementing and abrasion materials, fibers, foils, embedding materials and (contact) lenses by the silanes in accordance with the invention.

For constructing the anorganic network, the silanes in accordance with the invention or the polymer or polyaddition product of the inventive silanes are hydrolyzed and polycondensed, if necessary with the addition of other cocondensible components. Preferably, the polycondensation is carried out on the basis of the sol-gel-process as described, e.g. in German Patent specifications DE A1 2,758,414, 2,758,415, 3,011,761, 3,826,715 and 3,835,968.

For constructing the organic network, the silanes in accordance with the invention or the polycondensate of the of the inventive silanes is polymerized or subjected to polyaddition, if necessary with the addition of other copolymerizable components. The polymerization may be carried out thermally, by redox induction, photochemically or by complex-coordinated induction on the basis of processes as described, for instance, in German Patent specifications DE-A1 3,143,820, 3,826,715 and 3,835,968.

Radically and/or ionically polymerizable compounds may be added as additional polymerizable components. Radically polymerizable compounds suitable to be added are, e.g., those possessing C=C double bonds, such as, for instance, acrylates or methacrylates, with the polymerization taking place by way of the C=C double bonds. Ionically polymerizable compounds suitable to be added contain ring systems, for instance, which are cationically ring-scission polymerizable, such as, for instance, spiroorthoesters, spiroorthocarbonates, bicyclic spiroorthoesters, mono- or oligoepoxies. However, compounds may also be added which may be ionically as well as radically polymerizable, such as, for instance, methacryloyl-spiroorthoesters. They a radically polymerizable by way of the C=C double bond and cationically by ring-scission. The production of such systems has been described, for instance, in the Journal f. prakt. Chemie, volume 330, No. 2, 1988, pages 316–318. The silanes in accordance with the invention may also be used in systems of the kind described, for instance, in German patent specification 4,405,261.

Furthermore, it is possible to add other known silane-bonded cyclic systems which are included into the polymerization. Such systems contain epoxy groups, for instance.

The silanes in accordance with the invention may also be converted into macromulecular compounds by polyaddition (e.g., thiol addition). In the same manner, it is possible to carry out the polyaddition following the hydrolytic condensation of the inventive silanes. If, for instance, the thiol to be added contains at least two mercapto groups, it is possible to construct a multi-dimensional organic network. If hydrolyzable thiosilanes are used in the polyaddition, a multi-dimensional network will already be constructed if only one mercapto group is present in the thiosilane. The general reaction patterns is as follows:

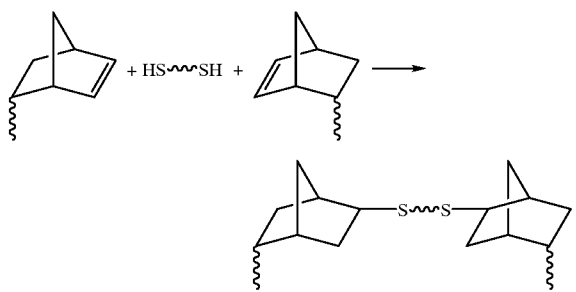

Without restriction of generalities, the following are examples of multi-thiols:

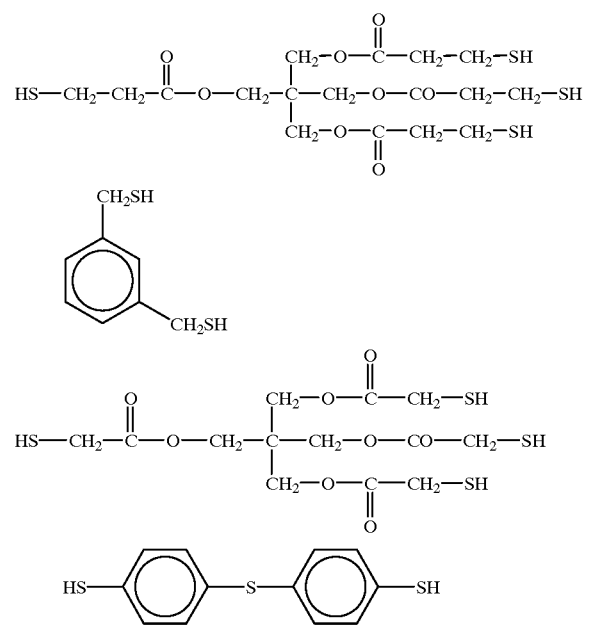

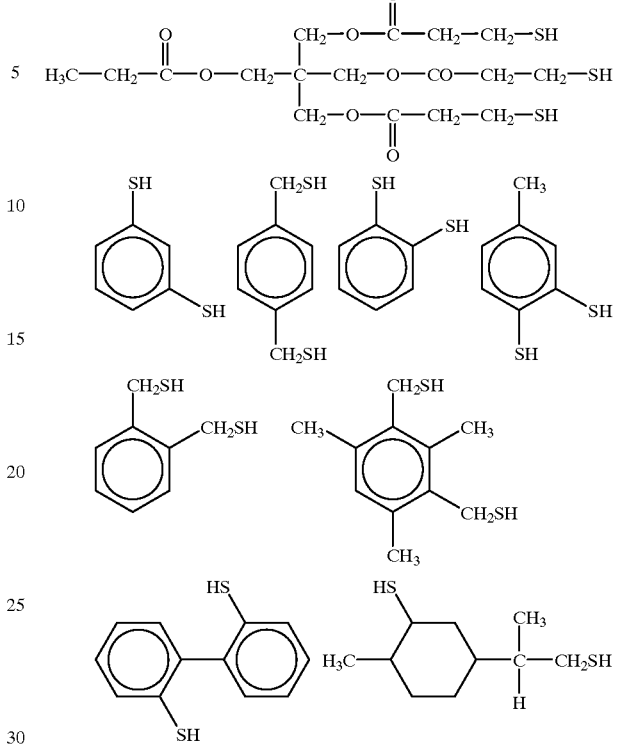

$H_3C$—$CH(SH)$—$CH_2SH$, $H_3C$—$CH(SH)$—$CH(SH)$—$CH_3$, $HSCH_2$—$CH_2$—$S$—$CH_2$—$CH_2SH$ and $HS$—$(CH_2)_n$—$SH$ with n=2 to 9.

The use of hydrolyzable silanes provided with mercapto groups as thiols, yields the advantage that such silanes may be incorpoarted into the organic network by way of the thiol-en-addition, and into the anorganic network by way of the hydrolytic condensation. It is thus possible to vary the cross-link density of the polycondensates or of the polyadducts and to adjust them to the requirements of any given application. Such silanes may be made by conventional methods. The following are concrete examples are given without restriction of generalities: $SH$—$(CH_2)_3$—$Si(OC_2H_5)_3$, $HS$—$(CH_2)_3$—$SiCH_3(OCH_3)_2$ and $HS$—$(CH_2)_3$—$Si(CH_3)_2(OC_2H_5)$.

It has surprisingly been found that silanes containing at least two thiol groups and corresponding to the general formula XV are especially well suited for the cross-linking of silanes in accordance with the invention or of polycondensates prepared from these silanes.

$$[(HS-R^5)_nR^6-S-E-R^5]_aSiX_xR^3_{4-a-x} \quad (XV)$$

The groups and indices of the general formula XV are equal are different and have the following meaning:

E=—CO—NH—, —CS—NH—, —CH$_2$—CH$_2$— or —CH$_2$—CH(OH)—;

$R^3$=alkyl, alkenyl, aryl, alkylaryl, or arylalkyl each with 1 to 15 C atoms, whereby these groups may be interrupted by oxygen or sulfur atoms, by ester, carbonyl, amide or amino groups;

$R^5$=alkene, arylene, arylenealkene, or alkenearylene each with 1 to 15 C atoms, whereby these groups may be interrupted by oxygen or sulfur atoms, by ester, carbonyl, amide or amino groups;

$R^6$=alkene, arylene, arylenealkene or alkenearylene each with 1 to 15 C atoms, whereby these groups may be interrupted by oxygen or sulfur atoms, by ester, carbonyl, amide or amino groups;

X=hydrogen, halogen, hydroxy, alkoxy, acyloxy, alkylcarbonyl, alkoxycarbonyl or NR″$_2$, wherein R″=Hydrogen, alkyl or aryl;

a=1, 2 or 3;

n=2, 3, 4 or 5;

x=1, 2 or 3.

Such oligothiolsilanes are not known and are particularly well suited for thiol-en-additions. The silanes of general -continued

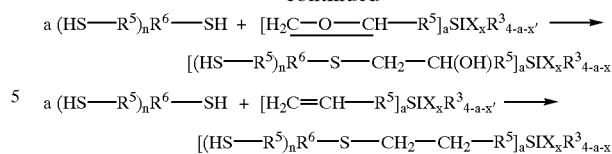

A concrete example is, without restriction of generality:

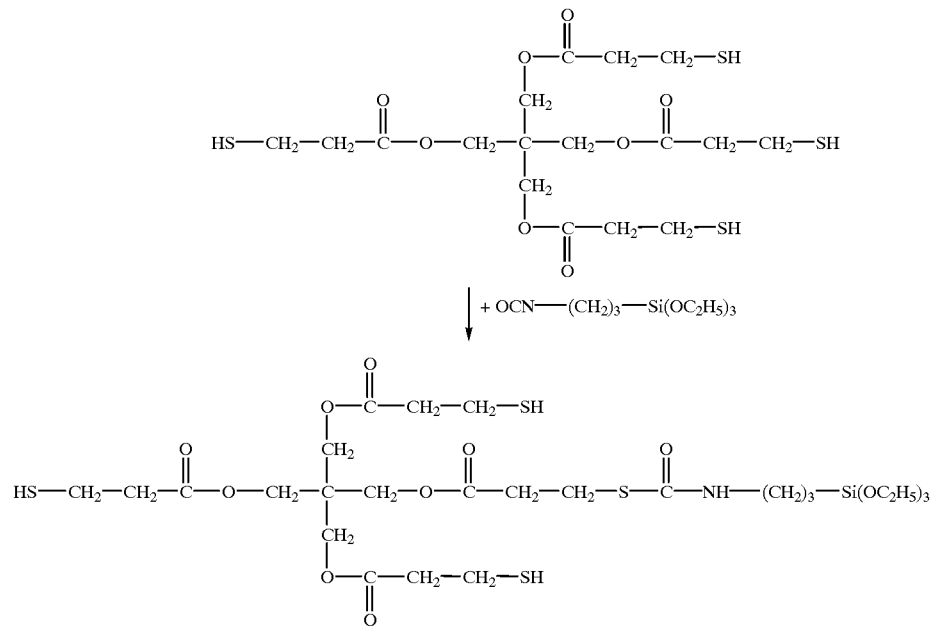

formula XV are condensible by the X groups, and they are (poly)additive by the thiol groups. They may be incorporated into an anorganic network by way of the hydrolytic condensation, and into an organic network by way of the polyaddition. The silanes of general formula XV may by themselves or in combination with other cocondensible compounds be processed by conventional methods, e.g. by a sol-gel process, into (hetero) silicic acid polycondensates which may subsequently be cross-linked by polyaddition, e.g., a thiol-en-addition. However, the silanes of general formula XV may also be processed by a polyaddition, e.g. a thiol-en-addition, to polyadducts which may subsequently be cured further by hydrolytic condensation.

The silanes of general formula XV may be produced on the basis of the following reaction patterns. Oligothiols are added to silanes the organic group(s) of which contain isocyanate, thioisocyanate or epoxy groups or C=C double bonds. Such silanes are commercially available or may be produced by methods described, for instance, in "Chemie und Technologie der Silicone" (W. Noll, Verlag Chemie GmbH., Weinheim/Bergstrasse, Germany, 1968).

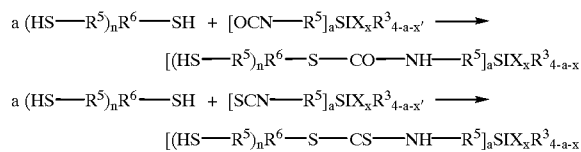

The silanes in accordance with the invention are highly reactive systems leading to poly(hetero)condensates which when irradiated, for instance, by ultra-violett radiation produce mechanically stable coatings or molded or filler articles. The silanes in accordance with the invention may be produced by simple addition and condensation reactions, and by an appropriate selection of the starting compounds, they may be proided with a variable number of reactive groups of differend functionality.

In the presence of two or more bicyclic groups and/or by the use of multi-thiols it is possible to construct a three-dimensional organic network. The mechanical properties (e.g. flexibility) and the physico-chemical properties (adsorption, refractive index, adhesion, etc.) of the (hetero) polycondensates may be influenced and adjusted in accordance with given applications by way of the spacing between Si atoms and the bicyclic group, i.e. by way of the length of the polymer chain, and by the presence of further functional groups within the chain. The aliphatic groups lead to flexible products, and the aromatic groups lead to rigid products. The cross-link density may be adjusted by the number of groups capable of cross-linking (SH groups and, for instance, norbornene groups) which thus also influence the properties and, hence, the possibilities of use of the poly(hetero)condensates.

Depending upon the type and number of hydrolyzable groups (e.g. alkoxy groups) silicon or glassy properties of the (hetero)polycondensates may be adjusted by the formation of an anorganic network.

The silanes in accordance with the invention are of a relatively high molecular weight and, hence, of a proportionally reduced volatility, resulting in lower toxic hazards during processing and application. In the course of the anorganic and/or organic cross-linking polysiloxanes of further reduced volatility are formed.

If the possibilities of varying the cocondensible and copolymerizable or coadditive components are additionally taken into consideration, it becomes apparent that the silanes in accordance with the invention produce silicic acid (hetero)polycondensates which in manifold ways may be adjusted to given fields of application, and which thus be used in all fields in which silicic acid (hetero) polycondensates have hitherto been used; but they also open up new possibilities of use, e.g. in the fields of optics, electronics, medicine, optoelectronics, food packaging, etc.

The silanes or their polycondensates, polymers or polyadducts may either be used as such or in compounds containing additives appropriate for a given application, e.g. conventional laquer additives, solvents, fillers, photo initiators, thermic initiators, flow agents and pigments. The silanes in accordance with the invention or the silane-containing compounds are suitable, for instance, for producing coating materials, fillers or bulk materials, adhesives and injection molding compounds, fibers, particles, foils, bonding intermediates, mold forming materials and imbedding materials. Coatings and molded articles made from silanes in accordance with the invention offer the advantage of being photochemically structurable. Particular fields of use are, for example, the coating of substrates made of metal, plastic, paper, ceramic by submersion, pouring, brushing, spraying, electrostatic spraying, galvanic laquering etc., their use in optical, opto-electric or electronic components, the manufacture of fillers, fibers or foils, the manufacture of scratch-proof and/or abrasion-resistant corrosion protection coatings, the manufacture of molded articles, for instance by injection molding, casting, pressing, rapid photo-typing or extrusion, the manufacture of (contact) lenses and the manufacture of composites, for instance with fibers, fillers or woven textiles.

Aside from the inventive silanes of formula (I) additional hydrolytically condensible compounds of silicon, boron, aluminum, phosphorus, tin, lead, the transition metals, lanthanides or actinides may also be used. Such compounds may be drawn upon either by themselves or in a precondensed condition for the production of the polycondensates. Preferably, at least 10 mol-%, more particularly at least 80 mol-%, and specifically at least 90 mol-% based on monomeric compounds, of the starting materials for producing the silicic acid (hetero)polycondensates are silicon compounds.

In like manner, the silicic acid (hetero) polycondensates are preferable based upon at least 5 mol-%, e.g. 25 to 100 mol-%, more particularly 50 to 100 mol-% and specifically 75 to 100 mol-% based on monomeric compounds, of one or more of the silanes in accordance with the invention.

Among the hydrolytically condensible silane compounds which differ from those of general formula (I) and which may be used in certain circumstances, those of general formula VIII are particularly preferred, $$R_a(R''Z')_b SiX_{4-(a+b)} \quad (VIII),$$

in which groups R, R", X and Z' are equal or different and have the following meaning:
R=alkyl, alkenyl, aryl, alkylaryl or arylalkyl;
R"=alkene or alkenylene whereby these groups may be interrupted by oxygen or sulfur atoms or by —NH— groups;
X=Hydrogen, halogen, hydroxy, alkoxy, acyloxy, alkylcarbonyl, alkoxycarbonyl or $NR'_2$ wherein R'=hydrogen, alkyl or aryl;
Z'=halogen or an if necessary substituted amino, amide, aldehyde, alkylcarbonyl, carboxy, mercapto, cyano, alkoxy, alkoxycarbonyl, sulphonic acid, phosphoric acid, acryloxy, methacryloxy, epoxy or vinyl group;
a=0, 1, 2 or 3;
b=0, 1, 2 or 3, with a+b=1, 2 or 3.

Such silanes have been described, for instance, in German Patent 3,407,087. The alkyl groups are, for instance, straight-chain, cross-linked or cyclic groups with 1 to 20, preferably 1 to 10 carbon atoms, and low alkyl groups of 1 to 6 carbon atoms are particularly preferred. Particular examples are methyl, ethyl, n-propyl, I-propyl, n-butyly, s-butyl, t-butyl, n-pentyl, n-hexyl, cyclohexyl, 2-ethylhexyl, dodecyl and octadecyl.

The alkenyl groups are, for instance, straight-chain, cross-linked or cyclic groups having 2 to 20, preferably 2 to 10 carbon atoms, and low alkenyl groups having 2 to 6 carbon atoms are particularly preferred, as, for instance, vinyl, allyl, or 2-butenyl.

Phenyl, biphenyl and naphthyl are preferred aryl groups.

The alkoxy, acyloxy, alkylcarbonyl, alkoxycarbonyl and amino groups are preferably derived from the alkyl and aryl groups mentioned supra. Particular examples are methoxy, ethoxy, n- and I-propoxy, n-, i-, s- and t-butoxy, methylamino, ethylamino, dimethylamino, di-ethylamino, N-ethylanilino, acetyloxy, propionyloxy, methylcabonyl, ethylcarbonyl, methoxycarbonyl, ethoxy-carbonyl, benzyl, 2-phenylethyl and tolyl.

The mentioned groupos may, if required, support one or more substituents, e.g., halogen, alkyl, hydroxyalkyl, alkoxy, aryl, aryloxy, alkylcarbonyl, alkoxycarbonyl, furfuryl, tetrahydrofurfuryl, amino, alkylamino, dialkylamino, trialkylammonium, amido, hydroxy, formyl, carboxy, mercapto, cyano, nitro, epoxy, $SO_3H$ and $PO_4H_2$.

Among the halogens, fluorine, chlorine and bromine are the preferred ones.

Particular examples of hydrolytically condensible silanes of general formula (VIII) are:
$CH_3$—Sl—$Cl_3$, $CH_3$—Sl—$(OC_2H_5)_3$, $C_2H_5$—Sl—$Cl_3$, $C_2H_5$—Sl—$(OC_2H_5)_3$, $CH_2$=CH—Sl—$(OC_2H_5)_3$, $CH_2$=CH—Sl—$(OC_2H_4OCH_3)_3$, $(CH_3)_2$—Sl—$Cl_2$, $CH_2$=CH—Sl—$(OOCCH_3)_3$, $(CH_3)_2$—Sl—$(OC_2H_5)_2$, $(C_2H_5)_3$—Sl—Cl, $(C_2H_5)_2$—Sl—$(OC_2H_5)_2$, $(CH_3)_2(CH_2$=CH)—Sl—$Cl_2$, $(CH_3)_3$—Sl—Cl, $(t$—$C_4H_9)(CH_3)_2$—Sl—Cl, $(CH_3O)_3$—Sl—$C_3H_6$—NH—$C_2H_4$—NH—$C_2H_4$—$NH_2$, $(CH_3O)_3$—Sl—$C_3H_6$—SH, $(CH_3O)_3$—Sl—$C_3H_6$—NH—$C_2H_4$—$NH_2$, $(CH_3O)_3$—Sl—$C_3H_6$—Cl, $(CH_3O)_3$—Sl—$C_3H_6$—O—C(O)—C$(CH_3)$=$CH_2$, $(CH_3)_2(CH_2$=CH—$CH_2)$—Sl—Cl, $(C_2H_5O)_3$—Sl—$C_3H_6$—$NH_2$, $(C_2H_5O)_3$—Sl—$C_3H_6$—CN,

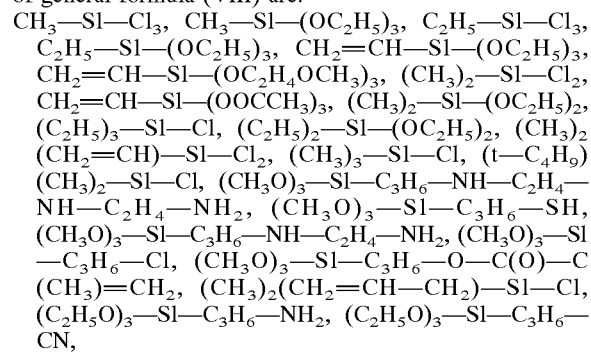

Among the hydrolytically condensible silicon compounds which differ from the silanes of general formula I and which may, if required, also be used, those of general formula IX are also preferred, $$\{X_n R_k Si[(R^2A)_l]_{4-(n+k)}\}_x B \quad (IX)$$

in which the groups A, R, $R^2$ and X are equal or different and have the following meaning:

A=O, S, PR", POR", NHC(O)O or NHC(O)NR" where R'=hudrogen, alkyl or aryl;

B=a straight-chain or cross-linked organic group derived from a compound B' having at least one (for l=1 and A=NHC(O)O or NHC(O)NR') or at least two C=C double bonds and 5 to 50 carbon atoms;

R=alkyl, alkenyl, aryl, alkylaryl or arylalkyl;

R$^2$=alkene, arylene or alkenearylene;

X=hydrogen, halogen, hydroxy, alkoxy, acyloxy, alkylcarbonyl, alkoxycarbonyl or NR'$_2$, where R'=hydrogen, alkyl or aryl;

n=1, 2 or 3;

k=0, 1 or 2;

l=0 or 1;

x=a whole integer the maximum value of which corresponds to the number of double bonds in the B' compound minus 1, or is equal to the number of double bonds in compound B' if l=1 and A is NHC(O)O or NHC(O)NR'.

Such silanes have been described in great detail in German Patent 4,011,044 and European Patent application EP 91,105,355.

For further processing into the poly(hetero)condensates, special isolation of the silanes in accordance with the invention is not necessary.

It is also possible initially to produce these silanes in bulk and thereafter, possibly by adding further hydrolyzable compounds, hydrolytically to condense them.

Among the possibly used aluminum compounds those of general formula AlR$^o{}_3$ are particularly preferred in which the groups R$^o$ which may be equal or different are selected from halogen, alkoxy, alkoxycarbonyl and hydroxy. As regards a more detailed (preferred) definition of these groups, reference may be made to the explanations relating to suitable hydrolyzable silicon compounds.

The groups just mentioned may also be totally or partially substituted by chelate ligands, e.g. by acetylacetone, acetoacetic acid ester, acetic acid or by carbonic acid derivatives of general formula

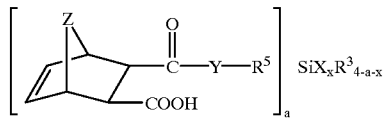

as explained in more detail in respect of the production of silanes in accordance with the invention. Particularly preferred aluminum compounds are aluminumalokoxides and aluminum halogenides. Concrete examples which may be mentioned in this context are: Al(OCH$_3$)$_3$, Al(OC$_2$H$_5$)$_3$, Al(O—n—C$_3$H$_7$)$_3$, Al(O—i—C$_3$H$_7$)$_3$, Al(OC$_4$H$_9$)$_3$, Al(O—l—C$_4$H$_9$)$_3$, Al(O—s—C$_4$H$_9$)$_3$, AlCl$_3$, and AlCl(OH)$_2$. Compounds which are liquid at room temperature, such as, e.g., aluminum-sec-butylate and aluminumisopropylate, are particularly preferred.

Suitable hydrolyzable titanium and zirconium compounds which may be used are those of general formula M$x_y$R$_z$ in which M is Ti or Zr, y is a whole integer between 1 and 4, particularly 2 to 4, and z is 0, 1, 2 or 3, preferably 0, 1 or 2, and X and R are defined as in the case of general formula I, whereby R is not, however, R$^2$—R$^1$—R$^4$—SiX$_x$R$^3{}_{3-x}$. This is also true for the preferred definitions. Especially preferred are compounds in which y equals 4.

As in the case of the aluminum compounds, complexed Ti and Zr compounds may also be used. Additionally preferred complex forming agents in this context are acrylic acid and methacrylic acid The following are examples of usable Zr and Ti compounds:

TiCl$_4$, Ti(OC$_2$H$_5$)$_4$, Ti(OC$_3$H$_7$)$_4$, Ti(O—i—C$_3$H$_7$)$_4$, Ti(OC$_4$H$_9$)$_4$, Ti(2-ethylhexoxy)$_4$, ZrCl$_4$, Zr(OC$_2$H$_5$)$_4$, Zr(OC$_3$H$_7$)$_4$, Zr(O—i—C$_3$H$_7$)$_4$, Zr(OC$_4$H$_9$)$_4$, Zr(2-ethylhexoxy)$_4$, ZrOCl$_2$.

Further hydrolyzable compounds which may be used for the production of (hetero)polycondensates are, for instance, borontrihalogenides and boric acid esters, such as, e.g., Bcl$_3$, B(OCH$_3$)$_3$, and B(OC$_2$H$_5$)$_3$, stannous tetrahalogenides and stannous tetraalkoxides, such as, e.g., SnCl$_4$ and Sn(OCH$_3$)$_4$, and vanadyl compounds, such as, e.g., VOCl$_3$ and VO(OCH$_3$)$_3$.

As has already been mentioned, the (hetero)polycondensates may be produced by processes common in this field. If, for practical reasons, silicon compounds are used exclusively, the hydrolytic condensation may in most cases by accomplished by adding the required water (preferrably with a stirring action and in the presence of a hydrolysis and condensation catalyst) at room temperature or slightly refrigerated, to the silicon compounds to be hydrolyzed either as such or in a suitable solvent, and by stirring the resulting mass for some time (one to several hours).

A step-wise addition of water is recommended when reactive compounds of Al, Ti or Zr are present. The hydrolysis is usually taking place, independently of the reactivity of the compounds present, at temperatures between −20 and 130° C. preferrably between 0 and 30° C. or at the boiling point of the solvent used. As has already been mentioned, the best way of adding water is primarily dependent upon the reactivity of the starting compounds. For instance, the dissolved starting compounds may be added in a drop-like manner to an excess of water, or the water is added to the dissolved compounds in one lot or in several portions. It may also be useful, instead of adding water as such, to add is by means of hydrous organic or anorganic systems into the reaction system. In many cases, the addition of the water into the reaction mixture by means of damp or wet adsorbers, e.g. by a molecular sieve, and of hydrous organic solvents, e.g. 80% ethanol, was found to be particularly suitable. However, water may also be added by a chemical reaction during the course which water is released. Esterifications are examples thereof.

Where solvents are used, aside from the low aliphatic alcohols (e.g. ethanol or I-propanol), ketones, preferably low dialkylketones, such as acetone or methylisobutylketone, ether, preferably low dialkylether such as diethylether or dibutylether, THF, amide, ester especially acetic acid ethyl ester, dimethylformamide, amines, especially triethylamine and other mixtures may be used.

The starting compounds need not necessarily all be present at the start of the hydrolysis (polycondensation), but in certain circumstances it may even be advantageous if initially only some of these compounds are brought into contact with water, and if the remaining compounds are added later on.

In order to prevent as much as possible precipitations during the hydrolysis and polycondensation when hydrolyzable compounds different from silicon compounds are used, water may be added in several steps, e.g. in three steps. For instance, one tenth to one twentieth of the water required for the hydrolysis may be added during the first step. After brief stirring, one fifth up to one tenth of the required amount of water may be added, and the remaining water may be added after another brief stirring.

The condensation time is dependent upon the individual starting compounds and the quantitative shares, the catalyst, if one is used, the reaction temperature, etc. In general, the polycondensation is carried out at normal pressure; it may, however, also be performed at increased or decreased pressure.

The resultant (hetero)polycondensate may either be processed further in the condition in which it was obtained, or after partial of complete removal of the used solvent. In some cases, it may be advantageous to replace the excess water or the resulting or the possibly additionally used solvent by another solvent in order to stabilize the (hetero)polycondensate. For this purpose the reaction mixture may be thickened to the point, e.g. in a vacuum at a slightly raised temperature, where it can still absorb another solvent without difficulty.

If these (hetero)polycondensates are to be used as lacquers for coating (e.g. plastics such as PVC, PC, PMMA, PE, PS, etc. or glass, paper, wood, ceramic, metal, and so forth), the usual lacquer additives such as, e.g., coloring agents (pigments and dyes), fillers, oxidation inhibitors, flame retardants, flow agents, UV absorbers, stabilizers and the like. Also to mentioned in this context are additives for raising the conductivity (e.g. graphite powder, silver powder etc.) When they are to be used as molding compounds, anorganic or organic fillers such as, for instance, organic or anorganic particles, minerals, fibers, fiberglass, etc. may be added.

The final curing of the (hetero)polycondensates will be carried out by polyaddition (e.g. thiol-en-addition) and/or thermically, by redox induction or photochemically after adding suitable initiators. Additional curing methods may take place at the same time and/or sequentially. During curing, the C=C double bonds are cross-linked in the course of a ring-scission polymerization or of a polyaddition, and the organic network is formed. Because of the relatively high molecular weights of the silanes in accordance with the invention or because of the specific reaction mechanisms during curing, i.e. the thiol-en-polyaddition, the volume of the silanes will only shrink very insignificantly.

The addition of further ionic and/or radically polymerizable components to the (hetero)polycondensates is also possible prior to the final curing, i.e. prior to the polymerization or polyaddition. Radically polymerizable compounds which may be added are, for instance, those with C=C double bonds, such as acrylates or methacrylates, with the polymerization taking place by way of the C=C double bonds. Ionically polymerizable compounds which may be added contain ring systems which are ionically ring-scission polymerizable, such as, for instance, spiroorthoesters, spiroorthocarbonates, bicyclic spiroorthoesters, mono- and oligoepoxies. However, it is also possible to add compounds which are polymerizable lonically as well as radically, such as, e.g., methacryloyl-spiroorthoesters. These are radically polymerizable by way of the C=C double bonds, and they are ionically polymerizable by ring-scission. Such systems have been described, for instance, in the Journal f. prakt. Chemie, volume 330, number 2, 1988, pages 316–318 or in the Journal of Polymer Science: Part C: Polymer Letters, Vol. 26, pages 517–520 (1988).

If curing of the (hetero)polycondensate is taking place photochemically, photo initiators will be added. With thermic curing thermal initiators will be added, and redox induced curing requires starter-activator systems. The initiator may be added in conventional quantities. Thus, a quantity of initiators, for instance, 0.5 to 5% by weight, more particularly 1 to 3% by weight, based on the mixture, may be added to a mixture containing 30 to 50% by weight of solids (polycondensate).

If aside from the silanes in accordance with the invention further components containing reactive double bonds, such as those of general formula IX, are used for producing the (hetero)polycondensates, a thermically, photochemically and/or redox-initiated polymerization may also take place by way of the double bonds.

The applicable photoinitiators may, for instance, be those commercially available. Examples thereof include Irgacure 184 (1-hydroxycyclohexylphenylketone), Irgacure 500 (1-hydroxycyclohexylphenylketone/benzophenone) and other photoinitiators of the Irgacure type available from the Ciba-Geigy company; Darocure 1173, 1116, 1398, 1174 and 1020 (available from the Merck company), benzophenone, 2-chlorothioxanthone, 2-methylthioxanthone, 2-isopropylthioxanthone, benzoine, 4,4'-dimethoxybenzoine, etc. If curing is carried out under visible light camphorchionone may be used as an initiator.

Particularly useful thermic initiators are organic peroxides such as diacylperoxides, peroxydicarbonates, alkylperesters, dialkylperoxides, perketalenes, ketone-peroxides and alkylhydroperoxides. Concrete and preferred examples of thermic initiators are dibenzoylperoxide, t-bytylperbenzoate and azobisisobutyronitrile.

The usual starter-activator systems may be applied as initiators or, as a starter, dibenzoylperoxide, for instance. The curing time may be set in accordance with a given application by the concentration or the ratio of concentration of these systems. Further amines are described in German patent 4,310,733, for instance.

Compounds with at least one amino group are, for instance, added as initiators in case of covalent-nucleophilic curing. Suitable amines are described in German patent 4,405,261, for instance.

A lacquer (hetero)polycondensate) based on silanes in accordance with the invention and provided with an initiator may be used for coating substrates. Conventional coating methods may be used for the coating, such as submersion, flooding, pouring, spinning, rolling, spraying, brushing, electrostatic spraying and galvanic lacquering. It is to be mentioned that the lacquer need not necessarily contain a solvent. Especially when using starter compounds (silanes) having two alkoxy groups on their Si atom, it is possible to operate without adding solvents.

Prior to curing, the applied lacquer should preferably be dried. Thereafter, it may be cured in a known manner, depending upon the kind of initiator, by redox induction, thermically or photochemically. Other combinations of curing methods are also possible, of course.

If the lacquer is cured by irradiation, it may be advantageous, after curing by radiation to carry out thermic curing, particularly to remove any solvents and to involve further reactive groups in the curing process.

Even though polymerizable groups are already present in the (hetero)polycondensates on the basis of the silanes in accordance with the invention, it may in certain circumstances of advantageous to add further compounds (preferably purely organic ones) having unsaturated groups, for instance, to these condensates prior to or during their further processing (curing). Preferred examples of such compounds are acrylic acid and methacrylic acid as well as compounds derived therefrom, in particular esters of preferably monovalent alcohols (e.g. $C_{1-4}$-alcanols, (meth)acrylnitril, styrene and mixtures thereof. Where the (hetero)polycondensates are used for producing coating lacquers such compounds may at the same time act as solvents and thinners.

The production of molded articles or molding compounds from (hetero)polycondensates on the basis of silanes in accordance with the invention may be accomplished by any method practiced in this field, such as, e.g., pressing, injection molding, casting, extrusion, etc. The (hetero) polycondensates based upon the silanes in accordance with the invention may also by used for producing composite materials (e.g. fiberglass reinforcement).

A further possible use of silanes in accordance with the invention resides in the production of hydrolytically condensible macro-molecular masses. To this end, the inventive silanes are subjected to polymerization and/or polyaddition, either by themselves or with radically and/or ionically polymerizable compounds. Final curing will thereafter be carried out by hydrolytic condensation by way of hydrolyzable groups of the inventive silanes and possibly further hydrolyzable components. In that case the organic network is first formed by polymerization or polyaddition, and thereafter the anorganic network is formed by hydrolytic condensation.

SUPPORTIVE EXAMPLES

The use of the silanes in accordance with the invention will be explained in detail on the basis of practical examples.

Example 1

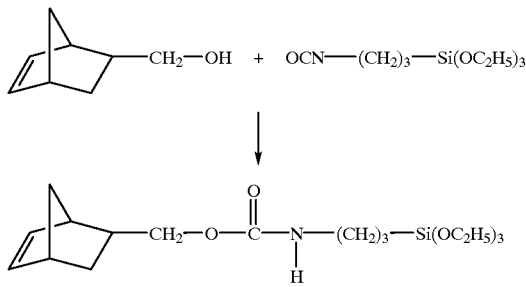

In a dry atmosphere, 30 mg of DBTL used as a catalyst and 12.4 g (50 mmol) of 3-isocyantopropyltriethoxysilane are added in drops to 6.2 g (50 mmol) of 2-(hydroxymethyl)-5-norborene. The conversion may be observed by way of the reduction of the isocyanate band in the infrared spectrum at 2272 cm$^{-1}$ and by the formation and increase of the urethane band at 1701/1723 cm$^{-1}$. The desired liquid product is obtained after stirring at room temperature for about one hour and may be used for further conversions without cleaning.

IR data:

$\upsilon_{(NH\ \ urethane)}$=3342 cm$^{-1}$ $\upsilon_{(C=O\ \ urethane)}$=1701/1723 cm$^{-1}$ $\upsilon_{(CH\ **\ olefine)}$=3059 cm$^{-1}$

Example 2

(Hydrolysis/condensation of the product of Example 1)

For the hydrolysis and condensation of its ethoxy groups the product of Example 1 is mixed with 2.2 g of water (+cat.) in 50 ml of acetic ester and thereafter stirred. Following complete conversion (proof by way of H$_5$O titration) the solution may after adding an equimolar amount (relative to the SH groups) of a thiol component be used for coating (with subsequent curing=thiol-en-polyaddition) any desired substrates.

Example 3

(Hydrolysis/condensation of the product of Example 1 after adding a further silane)

After adding 16.0 g (100 mmol) of vinylmethyldiethoxysilane in 50 ml acetic ester to the product of Example 1 (100 mmol) it is mixed and stirred with 2.2 g of water (+cat.) for hydrolysis and condensation. Following complete conversion (proof by H$_2$O titration) and after adding an equimolar amount (relative to the SH groups) of a thiol component, the resulting solution may be used, for instance, for coating (with subsequent curing=thiol-en-polyaddition) any desired substrate. Furthermore, after preparation and removal of solvent a liquid resin is obtained (solvent-free application is, therefore, possible) and after an appropriate addition of a thiol component and curing, it may be used for producing molded articles.

Example 4

(Hydrolysis/condensation of the product of Example 1 after addition of a vinylsilane and a reactive solvent)

For the hydrolysis and condensation of its ethoxy groups the product of Example 1 is mixed with 2.2 g of water (+ cat.) in 50 ml acetic ester after adding 16.0 g (100 mmol) of vinylmethyldiethoxysilane, and stirred. Following complete conversion (proof: 20 mmol of 1.12 dodecandioldemethacrylate as reactive thinner are added by H$_2$O titration). After adding an equimolar quantity (relative to the SH groups) of a thiol component, the resultant solution may be used for coating (followed by curing=thiol-en-polyaddition) of any desired substrates. Furthermore, after preparation and removal of solvent a liquid resin is obtained (solvent-free application is thus possible). After adding a thiol component and curing the resin may be used for producing molded articles. Because of the presence of methacrylate groups, curing (polymerizing the methacrylate groups) may also take place without the addition of thiol.

Example 5

(Thiol-en-polyaddition using the resin of Example 4)

2.3 g (12 mmol, equimolar ratio between SH— and C=C groups) of 1.9-nonandithiol as a thiol component and 1% Irgacure 184 (UV initiator from Ciba-Geigy Co.) are dissolve in 4.2 g of the resin from Example 4 as the en-component, and the mixture is put into a curing mold. The double bonds and the SH groups react within the bounds of a UV induced radical polyaddition, whereby the resin is cured. To this end the sample is irradiated by a UV point light source from the Hönle Co. The result is transparent and very flexible molded articles.

Example 6

(Thiol-en-polyaddition using the resin of Example 4)

12 mmol (equimolar ratio between SH— and C=C groups) of pentaerythritoltetrakis-3-mercaptopropionate) as the thiol component and 1% Irgacure 184 (UV initiator from Ciba-Geigy Co.) are dissolved in 4.2 g of the resin of Example 4 as the en-component, and the mixture is poured into a curing mold. The double bonds and the SH groups react within the bounds of a UV induced radical polyaddition whereby the resin is cured. To this end it is irradiated by a UV point light source. The result is transparent molded articles of markedly reduced flexibility, i.e., articles harder than those of Example 5. A stronger cross-linkage is obtained by a thiol component having 4 SH groups than by the 1.9-nonandithiol of Example 5.

Example 7

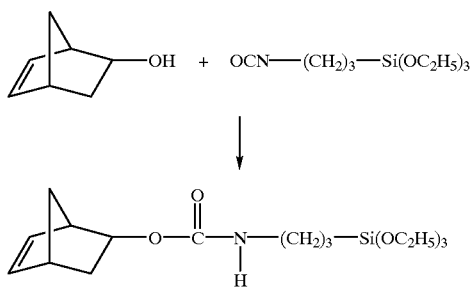

In dry atmosphere 63 mg of DBTL as catalyst and 24.7 g (100 mmol) of 3-isocyanatopropyltriethoxysilane are added by drops to 11.0 g (100 mmol) of 5-norbornene-2-ol. The conversion may be observed by the reducing isocyanate band in the IR spectrum at 2272 cm$^{-1}$ and by the formation and increase of the urethane band in the IR spectrum at 1700/1722 cm$^{-1}$. After stirring at room temperature for the desired product is obtained and may be used for further conversion without cleaning.

IR data:

$\upsilon_{(NH\ \ urethane)}$=3340 cm$^{-1}$ $\upsilon_{(C=O\ \ urethane)}$=1700/1722 cm$^{-1}$ $\upsilon_{(CH\ **\ olefine)}$=3064 cm$^{-1}$ $\delta_{(C=)}$=724 cm$^{-1}$

Example 8

(Hydrolysis and condensation of the product of Example 7)

For hydrolyzing and condensing the product of Example 7 (100 mmol) is mixed with 4.3 g of water (+ cat.) in 100 ml acetic ester, and stirred. After complete conversion (proof by H$_2$O titration) the solution may, after adding an equimolar amount (relative to the SH groups) of a thiol component, be used, for instance, for coating (followed by curing=thiol-en-polyaddition) any desired substrates.

Example 9

(Hydrolysis and condensation of Example 7 with an addition of a reactive solvent)

For hydrolyzing and condensing the product of Example 7 is mixed with 4.3 g of water (+ cat.) in 100 ml acetic ester, and stirred. After complete conversion (proof by H$_2$O titration) 40 mmol RapiCure DVE-3 (CH$_2$=CH—O—CH$_2$—CH$_2$—O—CH$_2$—CH$_2$—O—CH$_2$—CH$_2$—O—CH=CH$_2$) are added as reactive thinner. The resulting solution may after adding an equimolar amount (relative to the SH groups) of a thiol component be used for coating (followed by curing=thiol-en-polyaddition) any desired substrates. Furthermore, after preparation and solvent removal a liquid resin is obtained (hence, solvent free application is possible) which after an appropriate addition of a thiol component and after curing may be used for producing molded articles.

Example 10

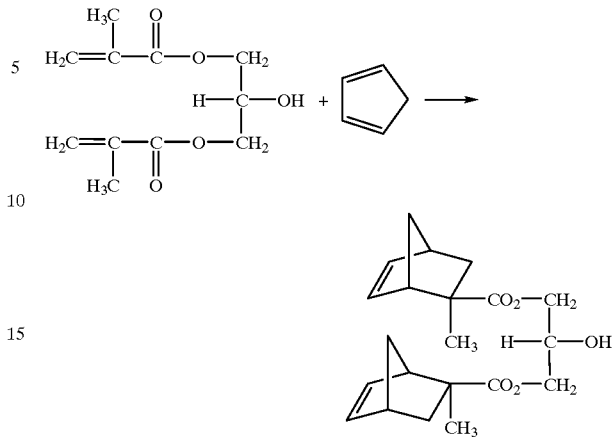

About 53 g (0.8 mol) of cyclopentadiene (freshly made by splitting dicyclopentadiene) are added by distillation to 68.5 g (0.3 mol) of glycerinedimethacrylate heated to 80° C. The conversion by Diels-Alder reaction may be observed by IR spectroscopy. Volatile components (e.g. non-converted cyclopentadiene) are removed after complete conversion of the methacrylate in order to obtain the desired liquid product. This may be used for further processing without cleaning.

IR data:

$\upsilon_{(OH)}$=3496 cm$^{-1}$ (broad)

$\upsilon_{(CH\ \ olefine)}$=3062 cm$^{-1}$ $\upsilon_{(C=O\ \ ester)}$=1730 cm$^{-1}$ $\upsilon_{(C=C)}$=1572 cm$^{-1}$ $\delta_{(C=C)}$=725 cm$^{-1}$

Example 11

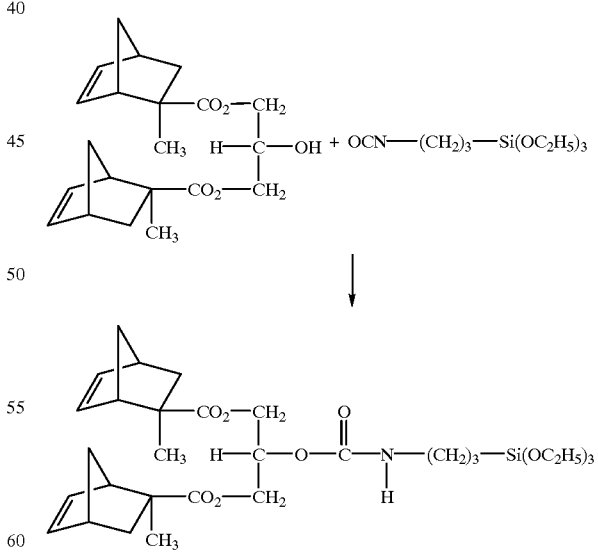

In a dry atmosphere 19.8 g (80 mmol) of 3-isocyanatopropyltriethoxysilane in THF as a solvent and DBTL as a catalyst are added in a drop-wise manner to 28.8 g (80 mmol) of the dinorbornene compound of Example 10. The conversion may be observed by the reduction of the isocyanate band in the IR spectrum at 2272 cm$^{-1}$ and by the formation and increase of the urethane band in the IR spectrum at 1733 cm$^{-1}$. After stirring at room temperature for about 2 hours the desired dissolved product may without cleaning be used for further conversion or be isolated after removal of the solvent.

IR Date:

$\upsilon_{(NH\ \ urethane)}$ 3380 cm$^{-1}$ $\upsilon_{(C=O\ \ urethane,\ ester)}$ ca. 1733 cm$^{-1}$ $\upsilon_{(CH\ **\ olefine)}$=3062 cm$^{-1}$ $\upsilon_{(C=C)}$=1572 cm$^{-1}$ $\delta_{(C=C)}$=725 cm$^{-1}$

Example 12
(Hydrolysis and condensation of the product of Example 11)

For hydrolyzing and condensing its ethoxy groups, the product solution of Example 11 (80 mmol) is mixed with 3.5 g of water (+ cat.) in 50 ml of acetic ester, and stirred. After complete conversion (proof by H$_2$O titration) 16 mmol of 1.12-dodecandioldimethacrylate are added as a reactive thinner. After adding an equimolar amount (relative to the SH groups) of a thiol component, the resultant solution may, for instance, be used for coating (followed by curing=thiol-en-polyaddition) of any desired substrates. Furthermore, after preparation and removal of solvent a liquid resin is obtained (solvent-free application is thus possible), which after adding a thiol component and after curing may be used for producing molded articles.

Example 14
(Thiol-en-polyaddition, using the resin of Example 13)

For hydrolyzing and condensing the product of Example 13 is mixed with 3.5 g of water (+ cat.) in 50 ml of acetic ester, and stirred. After complete conversion (proof by H$_2$O titration) 16 mmol of 1.12-dodecandioldimethacrylate are added as a reactive thinner. After adding an equimolar quantity (relative to the SH groups) of a thiol component, the resultant solution may be used for coating (followed by curing=thiol-en-polyaddition) any desired substrates. Furthermore, after preparation and removal of solvent, a liquid resin is obtained (solvent-free application is thus possible) which after an appropriate addition of a thiol component and after curing may be used, for instance, for producing molded articles.

Example 14
(Thiol-en-polyaddition, using the resin of Example 13, production of test articles to define mechanical characteristics)

A thiol component of 6 mmol (equimolar ratio between SH and C=C groups) of pentaerythritoltetrakis(3-mercaptopropionate) and 1% Irgacure 184 (UV initiator from Ciba-Geigy Co.) are dissolved in 5.64 g of the resin of Example 13 as the en-component and poured into a small stave mold (2×2×25 mm). The double bonds and the SH groups react within the bounds of a UV induced radical polyaddition whereby the resin is cured. To this end it is irradiated by a UV point light source from the Hönle Co. The E-module and the fracture strength of the resultant transparent small stave are defined by a three-point bending test. Because of the two norbornene groups per silane unit in the anorganic polymer structure, in combination with the 4 SH groups in the thiol component, a highly tight-meshed overall polymer structure results accompanied by a relatively high E-module. E-module and, with it, the flexibility are adjustable over wide ranges by way of the number of OR groups and of the norbornene groups within the silane and by way of the number of SH groups within the thiol component.

E-module=2000 MPa (±100)

Strength=90 MPa (±100)

Example 15
(Hydrolysis and condensation of the product of Example 11 and addition of the di-norbornene compound of Example 10 as reactive solvent)

For hydrolyzing and condensing the ethoxy groups, the product solution of Example 11 (50 mmol) is dissolved together with 10 mmol of the dinorbornene compound of Example 10 in 50 ml acetic ester, mixed with 3.5 g of water (+ cat.) and stirred at room temperature. After complete conversion (proof by H$_2$O titration) and preparation the resultant clear solution may, after adding an equimolar amount (relative to the Sh groups) of a thiol component, for instance be used for coating (followed by curing=thiol-en-polyaddition) any desired substrates. Furthermore, after removal of the solvent a liquid resin is obtained (solvent-free application is thus possible) which, after an appropriate addition of a thiol component and after curing may, for instance, be used for producing molded articles.

Example 16

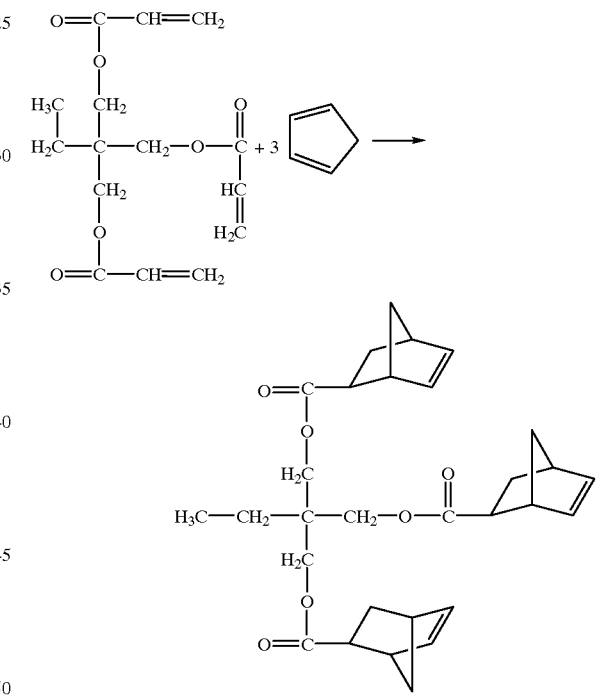

About 42.3 g (0.64 mol) of cyclopentadiene (freshly made by splitting dicyclopentadiene) are added by distilling to 59.3 g (0.2 mol) of trimethylolpropantriacrylate. The conversion by a Diels-Alder reaction may be observed by IR-spectroscopy. Volatile components (for instance, non-converted cyclopentadiene) are removed after complete conversion of the acrylate in order to obtain the desired liquid product. This may be used for further conversions without cleaning.

IR Date:

$\upsilon_{(CH\ \ olefine)}$=3061 cm$^{-1}$ $\upsilon_{(C=C\ \ ester)}$=1736 cm$^{-1}$ $\upsilon_{(C=C)}$=1570 cm$^{-1}$ $\delta_{(C=C)}$=712 cm$^{-1}$

Example 17

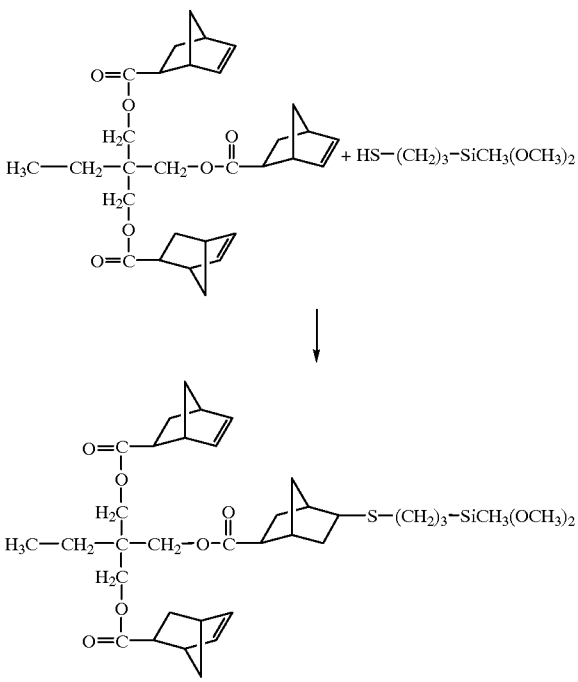

9.0 g (50 mmol) of mercaptopropylmethyldimethoxylane are added drop-wise under a protective gas atmosphere to 24.1 g (50 mmol) of the trinorbornene compound of Example 16 in 50 ml of acetic ester. After completion of the reaction (thiol addition) the desired product may be isolated by removing the solvent and be used for further conversions in this form or as a solution.

IR Data:

$\upsilon_{(CH ** olefine)}$=3061 cm$^{-1}$
$\upsilon_{(CH ** methoxy)}$=2835 cm$^{-1}$
$\upsilon_{(C=O ** ester)}$=1737 cm$^{-1}$
$\upsilon_{(C=C)}$=1570 cm$^{-1}$
$\delta_{(C=C)}$=712 cm−1

Example 18
(Hydrolysis/condensation of the product of Example 17)

For hydrolyzing and condensing the methoxy groups the product solution of Example 17 (50 mmol) are mixed in 1.4 g of water (+ cat.), and stirred. After complete conversion (proof by H$_2$O titration) the solution which is clear after preparation and after adding an equimolar amount (relative to the SH groups) of a thiol component may be used, for instance, for coating (followed by curing=thiol-en-polyaddition) any desired substrates. Furthermore, after removal of solvent a liquid resin is obtained (solvent-free application is thus possible) which after an appropriate addition of a thiol component and after curing may be used, for instance, for producing molded articles.

Example 19
(Hydrolysis/condensation of the product of Example 17 and addition of a reactive solvent)

The product solution of Example 18 (50 mmol) is mixed with 10 mmol 1.12-dodecandioldimethacrylate so that the resultant clear solution, after adding an equimolar amount (relative to the SH groups) of a thiol component, may be used, for instance, for coating (followed by curing=thiol-en-polyaddition) any desired substrates. Furthermore, after solvent removal a liquid resin is obtained (solvent-free application is thus possible) which after an appropriate addition of a thiol component and after curing may be used, for instance, for producing molded articles.

What is claimed is:

1. Hydrolyzable and polymerizable or polyadditive silanes of general formula (I)

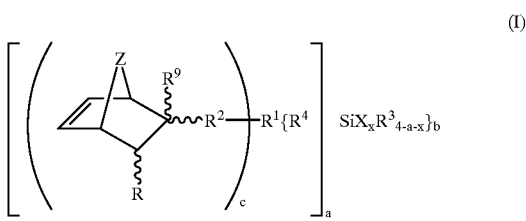

In which the groups and indices are identical or different and have the following meaning:

R=hydrogen, $R^2$—$R^1$—$R^4$—$SiX_xR^3_{3-x}$, carbonyl, alkyl, alkenyl, aryl, alkylaryl or arylalkyl each having 1–15 carbon atoms, whereby the groups may contain oxygen or sulfur atoms, ester, carbonyl, amide or amino groups;

R'=alkylene, arylene, arylenealkene or alkenearylene each with 0 to 15 carbon atoms, whereby these groups may contain oxygen or sulfur atoms, ester, carbonyl, amide or amino groups;

$R^2$=alkylene, arylene, arylenealkene or alkenearylene each having 0 to 15 carbon atoms, whereby these groups may contain oxygen or sulfur atoms, ester, carbonyl, amide or amino groups;

$R^3$=alkyl, alkene, aryl, alkylaryl or arylalkyl each with 1 to 15 carbon atoms, whereby these groups may contain oxygen or sulfur atoms, ester, carbonyl, amide or amino groups;

$R^4$=—(CHR$^6$—CHR$^6$)$_n$—, where n=0 or 1, —CHR$^6$—CHR$^6$—S—R$^5$—, —CHR$^6$—CHR$^6$—NR$^6$—R$^5$—, —Y—CS—NH—R$^5$—, —S—R$^5$, —Y—CO—NH—R$^5$—, —Y—CO—C$_2$H$_3$(COOH)—R$^5$—, —Y—CO—C$_2$H$_3$(OH)—R$^5$—;

$R^5$=alkylene, arylene, arylenealkene or alkenearylene each with 1 to 15 carbon atoms, whereby these groups may contain oxygen or sulfur atoms, ester, carbonyl, amide or amino groups;

$R^6$=hydrogen, alkyl or aryl with 1 to 10 carbon atoms;

$R^9$=hydrogen, alkyl, alkene, aryl, alkylaryl or arylalkyl each with 1 to 15 carbon atoms, whereby these groups may contain oxygen or sulfur atoms, ester, carbonyl, amide or amino groups;

X=hydrogen, halogen, hydroxy, alkoxy, acyloxy, alkylcarbonyl, alkoxycarbonyl or NR"$_2$, where R"=hydrogen, alkyl or aryl;

Y=—O—, —S— or —NR$^6$—;

Z=—O— or —CHR$^6$— or —(CHR$^6$)$_2$—;

a=1, 2 or 3, with b=1 for a=2 or 3;

b=1, 2 or 3, with a=1 for b=2 or 3;

c=1 to 6, with a+b+c>3 for Z=—O— and R≠R$^2$—R$^1$—R$^4$—SiX$_x$R$^3_{3-x}$, and with a+b+c>3 for Z=—CHR$^6$— and R≠R$^2$—R$^1$—R$^4$—SiX$_x$R$^3_{3-x}$ x=1, 2 or 3; and a+x=2, 3 or 4.

2. The silanes of claim 1 and general formula II,

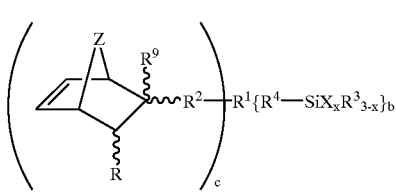
(II)

wherein index a in general formula I equals 1 and the groups and indices are defined as in claim 1.

3. The silanes of claim 1 and general formula III,

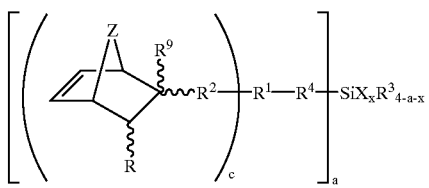
(III)

wherein index b in general formula I equals 1 and the groups and indices are defined as in claim 1.

4. The silanes of claim 1 and general formula IV,

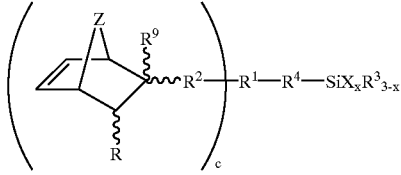
(IV)

wherein indices a and b in general formula I equal 1 and the groups and indices are defined as in claim 1.

5. The silanes of claim 1 and general formula V,

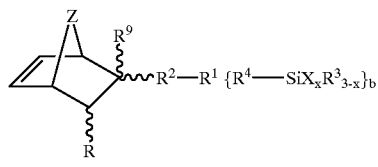
(V)

wherein indices a and c in general formula I equal 1 and the groups and indices are defined as in claim 1.

6. The silanes of claim 1 and general formula VI,

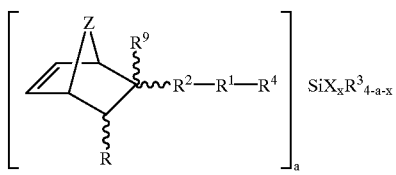
(VI)

wherein indices b and c in general formula I equal 1 and the groups and indices are defined as in claim 1.

7. The silanes of claim 1 and general formula VII,

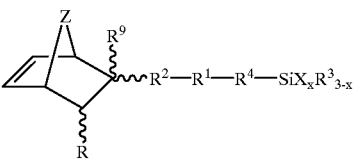
(VII)

wherein indices a, b and c in general formula I equal 1 and the groups and indices are defined as in claim 1.

8. The method of producing by silanes as defined in claim 1, organically modified silicic acid polycondensates or of organically modified hetero silicic acid polycondensates by hydrolytic condensation of at least one hydrolytically condensible compound of silicon and, optionally, of other elements of the group B, Al, P, Sn, Pb, the transition metals, the lanthanides and the actinides, and/or of precondensates derived from the above mentioned compounds, optionally in the presence of a catalyst and/or a solvent, under the influence of water or dampness, wherein 5 to 100 mol-% are selected on the basis of monomeric compounds of the hydrolytically condensible compounds of silanes of general formula (I)

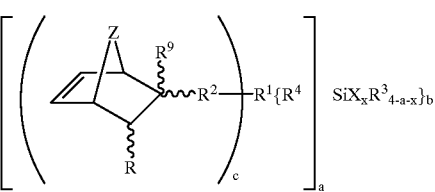
(I)

in which the groups and indices are defined as in claim 1.

9. The method of claim 8, wherein polyadditive and/or radically and/or jonically and/or covalent-nucleophillically polymerizable compounds are used as further hydrolytically condensible componds, optionally in precondensed form.

10. The method of use in accordance with claim 8, wherein at least one compound of general formula (VIII) is used as further hydrolytically condensible silicon compounds, if required in precondensed form, $$R_a(Z'R'')_b SiX_{4-(a+b)} \qquad (VIII)$$

in which the groups and indices have the following meaning:

R=alkyl, alkenyl, aryl, alkylaryl or arylalkyl;

R"=alkene or alkenylen, whereby these groups may be interrupted by oxygen or sulfur atoms or by amino groups;

X=hydrogen, halogen, hydroxy, alkoxy, acyloxy, alkylcarbonyl, alkoxycarbonyl or $NR'_2$, where R'=hydrogen, alkyl or aryl;

Z'=halogen or a, if necessary, substituted amino, amide, aldehyde, alkylcarbonyl, carboxy, mercapto, cyano, alkoxy, alkoxycarbonyl, sulphonic acid, phosphoric acid, acryloxy, methacryloxy, epoxy or vinyl group;

a=0, 1, 2 or 3;

b=0, 1, 2 or 3, with a+b=1, 2 or 3.

11. The method of claim 8, wherein at least one compound of general formula (IX) is used as further hydrolytically condensible compounds of silicon, optionally in precondensed form,

where the groups and indices have the following meaning:

A=O, S, PR', POR', NHC(O)0 or NHC(O)NR', where R'=hydrogen, alkyl or aryl;

B=a straight-chain or cross-linked organic group derived from a compound B' with at least one (for l=1 and A=NHC(O)O or NHC(O)NR' or at least two C=C double bonds and 5 to 50 carbon atoms, where R'=hydrogen, alkyl or aryl;

R=alkyl, alkenyl, aryl, alylaryl or arylalkyl;

$R^2$=alkylene, arylene or alkenearylene;

X=hydrogen, halogen, hydroxy, alkoxy, acyloxy, alkylcarbonyl, alkoxycarbonyl or $NR'_2$, where R'=hydrogen, alkyl or aryl;

n=1, 2 or 3;

k=0, 1 or 2;

l=0 or 1;

x=a whole integer the maximum value of which corresponds to the number of double bonds in compound B' minus 1, or is equal to the number of double bonds in the compound B1 if l=1 and A is NHC(O)O or NHC(O)NR'.

12. The method of claim 11, wher ein a compound of general formula (IX) is used in which the group B is derived from a substituted or unsubstituted compound B' with two or more acrylate and/or methacrylate groups.

13. The method of claim 8, wherein as further hydrolytically condensible compounds at least one of aluminum, titanium and zirconium compounds of formula $AlR°_3$ or $Mx_yR_z$ which are dissolvable in the reaction medium are used, in which M is titanium or zirconium, the groups R, R° and X are equal or different, R° is halogen, hydroxy, alkoxy or acyloxy, y is a whole integer from 1 to 4, particularly 2 to 4, z is 0, 1, 2 or 3, preferably 0, 1 or 2 and X and R are defined as in the general formula (I).

14. The method of claim 8, wherein at least one radically and/or ionically and/or covalent-nucleophillically polymerizable compound and/or polyadditive compounds is, optionally, added to the polycondensate and wherein the polycondensate is cured by polymerization or polyaddition.

15. The method of producing with silanes defined in claim 1, macromolecular materials by ring-scission polymerization of at least one cyclic compound provided with C=C double bonds and/or by polyaddition of thiols to one or more cyclic compounds provided with C=C double bonds, and, optionally, by radical and/or ionic and/or covalent-nucleophillic polymerization of further radically and/or ionically and/or covalent-nucleophillically polymerizable compounds and/or of oligomers derived from the compounds mentioned above, optionally by heating and/or electromagnetic radiation and/or by redox induction and, optionally in the presence of at least one initiator and/or a solvent, wherein 5 to 100 mol-% of the cyclic compound provided with C=C double bonds is selected on the basis of monomeric compounds from the silanes of formula (I)

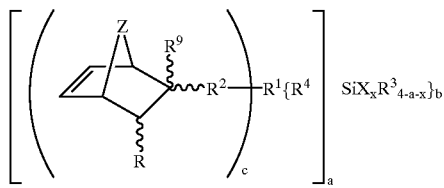

in which the groups and indices are defined as in claim 1.

16. The method of claim 15, wherein at least one spiroorthoester, spiroorthocarbonate, bicyclic spiroorthoester, methacryloyl-spiroorthoester, mono- or oligoepoxie is used as a kationic polymerizable compound.

17. The method of claim 15, wherein at least one compound of general formula IX

in which the groups and indices are defines as in claim 11, is used as a radically polymerizable compound.

18. The method of claim 15, wherein the polymer or the product of the polyaddition is hydrolycically condensed, optionally in the presence of further hydrolytically condensible compounds of silicon and, optionally of other elements from the group of B, Al, P, Sn, Pb, transitional metals, lanthanides and actinides and/or of precondensates derived from the compounds mentioned above, by the influence of water or humidity, optionally in the presence of a katalyst and/or solvent.

19. The method of claim 18, wherein at least one compound of genral formula (VIII)

in which the groups and indices are defined as in claim 10, is used, optionally in precondensed form, as further condensible compounds of silicon.

20. The method of producing with the silanes defined in claim 1, bulk materials, composites, adhesives, grouting and caulking compounds, coating materials, grinding materials coatings, bonding intermediates, fillers, fibers, foils, contact (lenses) and binding materials for particles.

21. The method of producing silanes as defined in claim 1, wherein 1 to b mols of a silane of formula HY—$R^5$—)$_a$SiXR$^3_{4-a-x}$ or H$^a$SiXR$^3_{4-a-x}$ are converted with a mols of a compound of one of formulae XI and XII,

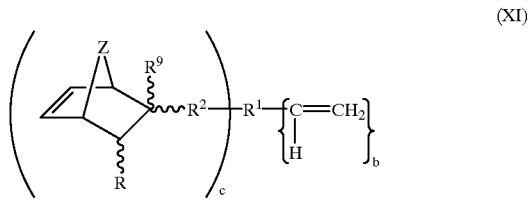

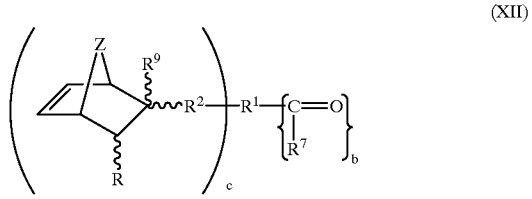

where $R^7$ is OH, OR, Cl or H, and the remaining groups and indices are defined as in claim 1.

22. The method of making silanes defined in claim 1, wherein 1 to b mols of a silane of formula $(R^8-R^5-)_a SiXR^3_{4-a-x}$ is converted with a mols of a compound of general formula XIII,

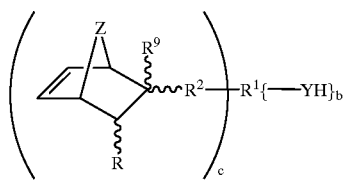

(XIII)

where $R^8$ is a thioisocyanate, isocyanate, epoxy or a cyclic anhydride group and the remaining groups and indices are defined as in claim 1.

23. The method of making silanes as defined in claims 1, wherein a silane of general formula $(HY-R^5-)_S SiXR^3_{4-a-x}$ is converted with a compound of general formula XIV

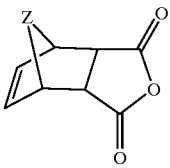

(XIV)

whereby the groups and indices are defined as in claim 1.

24. The method of making silanes as defined in claim 1, wherein a furane, cyclopentadiene or cyclohexadiene derivative is subjected in a Diels-Alder reaction to a silane of general formula $[(H_2C=CH-)_c R^1]_a SiX_x R4\text{-}a\text{-}x$, wherein the groups and indices are defined as in claim 1.

* * * * *